United States Patent [19]
Davis et al.

[11] Patent Number: 5,426,177
[45] Date of Patent: Jun. 20, 1995

[54] CILIARY NEUROTROPHIC FACTOR RECEPTOR

[75] Inventors: Samuel Davis, New York; Stephen P. Squinto, Irvington; Mark E. Furth, Pelham; George D. Yancopoulos, Briarcliff Manor, all of N.Y.

[73] Assignee: Regeneron Pharmaceuticals, Inc., Tarrytown, N.Y.

[21] Appl. No.: 676,647

[22] Filed: Mar. 28, 1991

Related U.S. Application Data

[63] Continuation-in-part of Ser. No. 532,285, Jun. 1, 1990, abandoned.

[51] Int. Cl.⁶ .............................................. C07K 13/00
[52] U.S. Cl. .................................... 530/395; 530/350; 530/839
[58] Field of Search ............... 530/350, 387.1, 388.1, 530/388.22, 827, 839, 395; 536/27; 435/6, 69.1, 172.3, 240.2, 7.1; 514/12

[56] References Cited

PUBLICATIONS

Seed et al. Molecular cloning of the CD2 . . . 1987. PNAS. USA. 84:3365–3369.
Lin et al. Purification, cloning, and expression . . . 1989. Science 246:1023–1025.
Munro et al. An Hsp70–like Protein in the . . . 1986. Cell 46:291–300.

Primary Examiner—Robert J. Hill, Jr.
Assistant Examiner—Sally P. Teng
Attorney, Agent, or Firm—Pennie & Edmonds

[57] ABSTRACT

The present invention relates to the ciliary neurotrophic factor (CNTF) receptor, and provides for CNTF receptor nucleic acid and amino acid sequences. It also relates to (i) assay systems for detecting CNTF activity; (ii) experimental model systems for studying the physiologic role of CNTF; (ii) diagnostic techniques for identifying CNTF-related neurologic conditions; (iv) therapeutic techniques for the treatment of CNTF-related neurologic and muscular conditions, and (v) methods for identifying molecules homologous to CNTF and CNTFR.

1 Claim, 11 Drawing Sheets

Figure 1A:
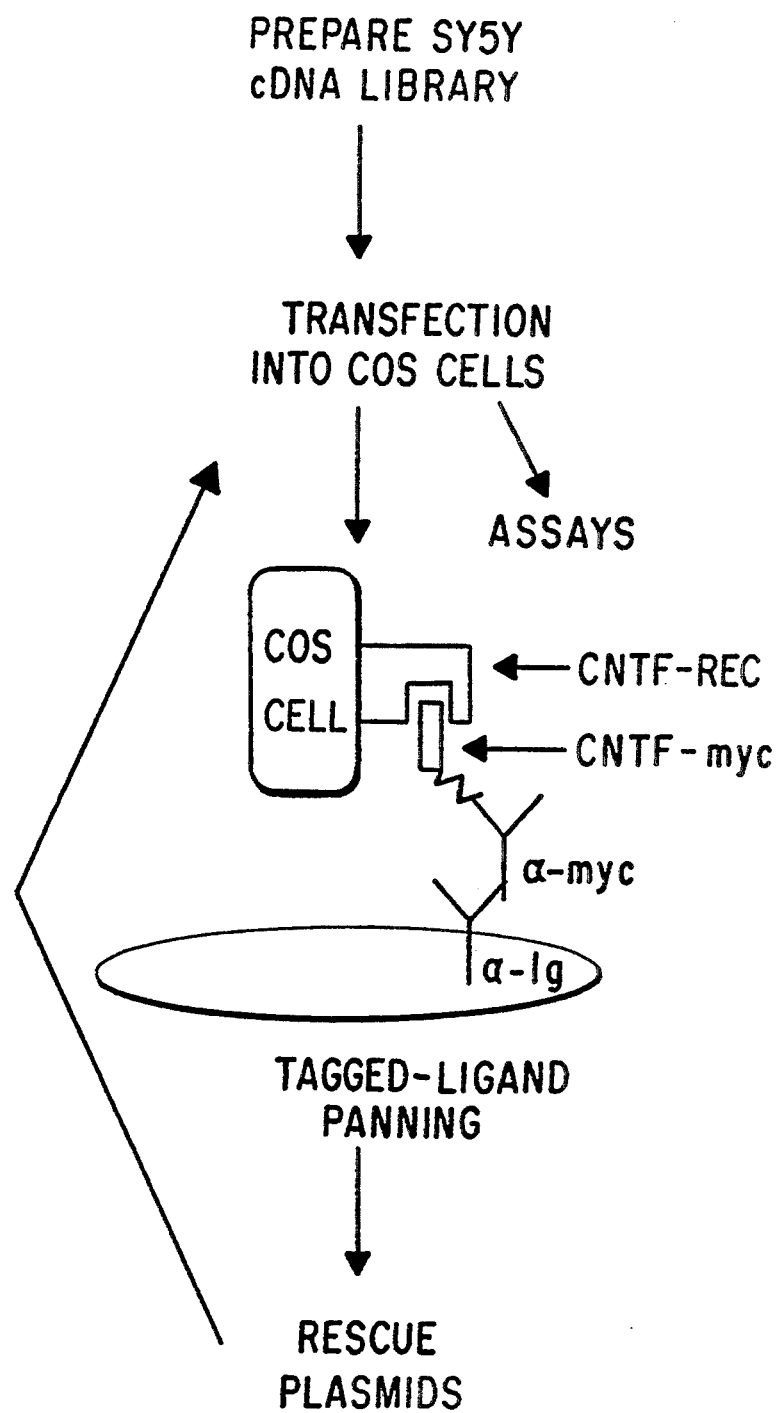

BEFORE PANNING
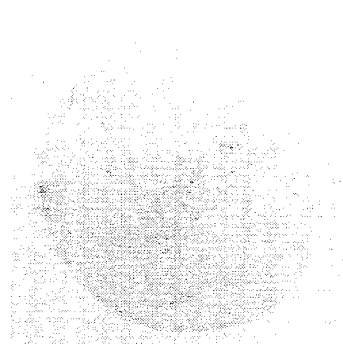
AFTER TAGGED-
LIGAND PANNING
FIG. 1B (i)   FIG. 1B (ii)
NEGATIVE
CLONE
POSITIVE
CLONE
FIG. 1C(i)   FIG. 1C(ii)
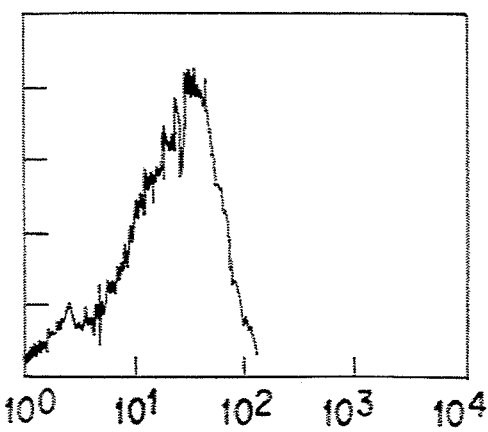
NEGATIVE CLONE
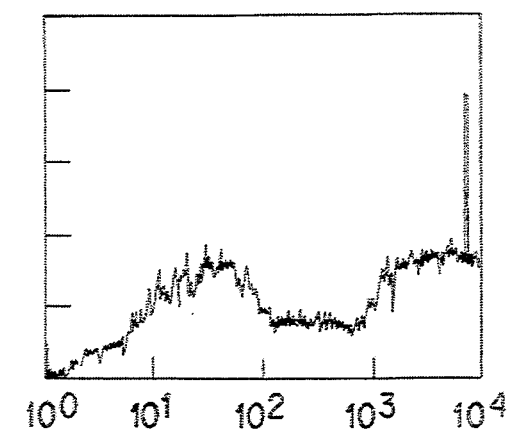
POSITIVE CLONE
FIG. 1D(i)   FIG. 1D(ii)

```
         10           20           30           40           50           60           70           80
CCTCGAGATC CATTGTGCTC AAAGGGCGGC GGCAGCGGAG GCGGCGGGCTC CAGCCGGGC GGCCCGGAGGC TCGGCGGTGG
GGAGCTCTAG GTAACACGAG TTTCCCGCCG CCGTCGCCTC CGCCGCCGAG GTCGGCGCCG CCGGCGCTCCG AGCCGCCACC
         90          100          110          120          130          140          150
GATCCGGCGG GCGGTGCTAG CTCCGCGCTC CCTGCCTCGC TCGCTGCCGG GGGCGGTCGG AAGGCGCGG
CTAGGCCGCC CGCCACGATC GAGGGCGGAG GGACGGAGCG AGCGACGGCC CCCGCCAGCC TTCCGGCGG 160          170          180          190          200          210          220          230
GCGAAGCCCG GGTGGCCCGA GGGCGCGACT CTAGCCTTGT CACCTCATCT TGCCCCCTTG GTTTTGGAAG TCCTGAAGAG
CGCTTCGGCG CCACCGGGCT CCCGCGCTGA GATCGGAACA GTGGAGTAGA ACGGGGAAC CAAAACTTC AGGACTTCTC
        240          250          260          270          280          290          300
TTGGTCTGGA GGAGGAGGAG GACATTGATG TGCTTGGTGT GTGGCCAGTG GTGAAGAG ATG GCT GCT CCT GTC
AACCAGACCT CCTCCTCCTC CTGTAACTAC ACGAACCACA CACCGGTCAC CACTTCTC                Met Ala Ala Pro Val>

310                  320                  330                  340                  350                  360
CCG TGG GCC TCG TGT GCT GTG CTT GCC GCC GCA GTT GTC TAC GCC CAG AGA CAC AGT CCA
GGC ACC CGG ACG ACA CGA CAC GAA CGG CGT CAA CAG ATG CGG GTC TCT GTG TCA GGT
Pro Trp Ala Cys Ala Val Leu Ala Ala Ala Ala Val Tyr Ala Gln Arg His Ser Pro
370                  380                  390                  400                  410                  420                  430
CAG GAG GCA CCC CAT GTG CTG GGC TAC GAG CGC CTG GTG ACA CTG CCA TGT GGG ACA
GTC CTC CGT GGG GTA CAC GAC CCG ATG CTC GCG GAC CCG AGA CTC CAC TGT GAC ACA CCC TGT
Gln Glu Ala Pro His Val Gln Tyr Glu Arg Leu Gly Ser Asp Val Thr Leu Pro Cys Gly Thr>

440                  450                  460                  470                  480                  490
GCA AAC TGG GAT GCT GCG GTG ACG TGG CGG GTA AAT GGG ACA GAC CTG GCC CCT GAC CTG CTC AAC
CGT TTG ACC CTA CGA CGC CAC CGC CAC TGC ACC GCC CAT TTA CCC TGT CTG GAC CGG GGA CTG GAC GAG TTG
Ala Asn Trp Asp Ala Ala Val Thr Arg Val Asn Gly Thr Asp Leu Ala Pro Asp Leu Leu Asn
500                  510                  520                  530                  540                  550                  560
GGC TCT CAG CTG GTG CTC CAT GGC CTG GAA CTG GAC CAC AGT GGC CAC CTG TAC GCC TTC CAC
CCG AGA GTC GAC CAC GAG GTA CCG GAC CTT GAC CTG TCA CCG GTG GAC ATG CGG ACG AAG GTG
Gly Ser Gln Leu Val Leu His Gly Leu Glu Leu Asp His Ser Gly His Leu Tyr Ala Cys Phe His>
```

FIG.2A

```
        570            580            590            600            610            620
CGT GAC TCC TGG CAC CTG CGC CAC CAA GTC CTG CTG CAT GTG GGC TTG CCG CCG CGG GAG CCT GTG
GCA CTG AGG ACC GTG GAC GCG GTT CAG GAC CAC GTA CAC CCG AAC CGG GCC CTC GGA CAC
Arg Asp Trp His Leu Arg His Val Gln Val Leu Leu His Val Gly Leu Pro Pro Arg Glu Pro Val
 630                            650                        670                680            690
CTC AGC TGC CGC TCC AAC ACT TAC CCC AAG GGC TTC TAC AGC TGC CAT CTG CCC ACC CCC
GAG TCG ACG GCG AGG TTG TGA ATG GGG TTC CCG AAG ATG AGG ACG TCG ACC GTA GAC TGG GGG
Leu Ser Cys Arg Ser Asn Thr Tyr Pro Lys Gly Phe Tyr Cys Ser Trp His Leu Pro Thr Pro〉
     700            710            720            730            740            750
ACC TAC ATT CCC AAC ACC TTC AAT GTG CTG ACT GTG CTG CAT GGC TCC AAA ATT ATG GTC TGT GAG AAG
TGG ATG TAA GGG TTG TGG AAG TTA CAC GAC TGA CAC GTA CCG AGG TTT TAA TAC CAG ACA CTC TTC
Thr Tyr Ile Pro Asn Thr Phe Asn Val Leu Thr Val Leu His Gly Ser Lys Ile Met Val Cys Glu Lys
 760                        770                    790                810
GAC CCA GCC CTC AAG AAC CGC TAC ATT CGC CAC ATG CAC CTG TTC TCC ACC ATC AAG TAC
CTG GGT CGG GAG TTC TTG CCG ATG TAA GCG GTG TAC GTG GAC AAG AGG TGG TAG TTC ATG
Asp Pro Ala Leu Lys Asn Arg Cys His Ile Arg Tyr Met His Leu Phe Ser Thr Ile Lys Try〉
 820            830            840            850            860            870            880
AAG GTC TCC ATA AGT GTC GCC AGC AAT GCC CTG GGC CAC AAT GCC ACA GCT ATC ACC TTT GAC GAG TTC
TTC CAG AGG TAT TCA CAG GCG TCG TTA CGG GAC CCG GTG TTA CGG TGT CGA TAG TGG AAA CTG CTC AAG
Lys Val Ser Ile Ser Val Ser Asn Ala Leu Gly His Asn Ala Thr Ala Ile Thr Phe Asp Glu Phe
 890                    910                    930                940
ACC ATT GTG AAG TTC CCA GAA AAT GTG GCC CGG CCA GTG CCC AGC AAC CCT CGC
TGG TAA CAC TTC AAG GGT CTT TTA CAC CGG GCC GGT CAC GGG TCG TTG GGA GCG
Thr Ile Val Lys Phe Pro Glu Asn Val Ala Arg Pro Val Pro Ser Asn Pro Arg〉
 950            960            970            980            990            1000            1010
CGG CTG GAG GTG ACG TGG CAG GTG ACC CCC ACC TCG GGG AGC GTC TGG CCT GAC CCT GAG TCT TTT CCT CTC AAG TTC
GCC GAC CTC CAC GTG ACC GTC CAC TGG GGG TGG AGC CCC TCG CAG ACC GGA CTG AGA AAA GGA GAG TTC AAG
Arg Leu Glu Val Thr Trp Gln Thr Pro Ser Thr Trp Pro Asp Pro Glu Ser Phe Pro Leu Lys Phe
```

FIG.2B

```
        1020          1030          1040          1050          1060          1070
TTT CTG CGC TAC CGA CCC CTC ATC CTG GAC CAG CAT GTG GAG CTG TCC GAC GGC ACA
AAA GAC GCG ATG GCT GGG GAG TAG GAC CTG GAC CTG GTA CAC CTC GAC AGG CCG TGT
Phe Leu Arg Tyr Arg Pro Leu Ile Leu Asp Gln His Val Glu Leu Ser Asp Gly Thr>

1080          1090          1100          1110          1120          1130          1140
GCA CAC ACC ATC ACA GAT CTA CGG ATG GCC TAC GCC GGG AAG GAG TAC ATT ATC CAG GTG GCA GCC AAG GAC AAT
CGT GTG TGG TAG TGT CTA GAT GCC TAC CGG ATG CGG CCC TTC CTC ATG TAA TAG GTC CAC CGT CGG TTC CTG TTA
Ala His Thr Ile Thr Asp Ala Tyr Ala Gly Ile Tyr Ala Gly Lys Glu Tyr Ile Ile Gln Val Ala Ala Lys Asp Asn
        1150          1160          1170          1180          1190          1200

GAG ATT GGG ACA TGG AGT GAC TGG AGC GTA GCC CAC GCT CGG GTG TGG ACT GAG GAA CCG
CTC TAA CCC TGT ACC TCA CTG ACA TCG CAT CGG GTG CGA TGC CAC TGA CTC CTT GGC
Glu Ile Gly Thr Trp Ser Asp Trp Ser Val Ala Ala His Ala Thr Pro Trp Thr Glu Glu Pro>

1210          1220          1230          1240          1250          1260          1270
CGA CAC CTC ACC ACG GAG GCC CAG GCT GCG CGC GAG GAC CTC TGG TCG ACC ACC AGC TCC CTG GCA CCC
GCT GTG GAG TGG CTC CGG GTC CGA CGC GCT CTG CTG GAG ACC AGC TGG TGG TCG AGG GAC CGT GGG
Arg His Leu Thr Glu Ala Gln Ala Ala Glu Asp Leu Trp Ser Thr Thr Ser Ser Leu Ala Pro
        1280          1290          1300          1310          1320          1330

CCA CCT ACC ACG AAG ATC TGT GAC CCT GGG GAG CTG GAC CCG TCG GGA CCC TCG GCA CCC
GGT GGA TGG TGC TTC TAG ACA CTG GGA CCC CTC GAC CTG GGC AGC CCT GGG AGC CGT GGG
Pro Pro Thr Thr Lys Ile Cys Asp Pro Gly Glu Leu Asp Pro Ser Gly Gly Pro Ser Ala Pro>

1340          1350          1360          1370          1380          1390          1400
TTC TTG GTC AGC GTC CCC ATC ACT CTG GCC CTG GCT GCC GCT GCC ACT GCC AGC AGT CTC TTG
AAG AAC ACA TCG CAG GGG TAG TGA GAC CGG GAC CGA CGG CGA CGG TGA CGG TCG TCA GAG AAC
Phe Leu Val Ser Val Pro Ile Thr Leu Ala Leu Ala Ala Ala Thr Ala Ser Ser Leu Leu
        1410          1420          1430          1440          1450          1460          1470

ATC TGAGCC CGGCACCCCA TGAGGACATG CAGAGGCACCT GCAGAGGAGC AGGAGGCCGG AGTGAGCCT
TAG ACTCGG GCCGTGGGGT ACTCCTGTAC GTCTCGTGGA CGTCTCCTCG TCCTCCGGCC TCGACTCGGA
Ile>
```

FIG. 2C

```
      1480       1490       1500       1510       1520       1530       1540       1550
GCAGACCCCG GTTTCTATTT TGCACACGGG CAGGAGGACC TTTGCATTC  TCTTCAGACA CAATTGTGTG AGACCCCGGC
CGTCTGGGGC CAAAGATAAA ACGTGTGCCC GTCCTCCTGG AAAACGTAAG AGAAGTCTGT GTTAAACACC TCTGGGGCCG
      1560       1570       1580       1590
GGGCCCGGGC CTGCCGCCCC CCAGCCCTGC CGCACCAAGC T
CCCGGGCCCG GACGGCGGGG GGTCGGGACG GCGTGGTTCG A
```

FIG.2D

|          |     |      |   |       |    |     |     |   |   |
|----------|-----|------|---|-------|----|-----|-----|---|---|
| hCNTFR   | 42  | VTLP | C | -8 aa- | V  | W   | --  | R | V |
| hIL6R    | 43  | VTLT | C | -10aa- | V  | W   | VL- | R | K |
| hCEA     | 611 | LNLS | C | -9 aa- | Y  | W   | --  | R | I |
| PDGFR    |     | ITIR | C | -9 aa- | F  | Q   | TYP | R | M |
| CSF-1R   |     | AQIV | C | -8 aa- | F  | D   | SL- | R | H |
| ALPHA1 B-GP | | VTLT | C | -8 aa- | F  | L   | --  | R | R |

|          |   |   |          |   |   |   |   |   |
|----------|---|---|----------|---|---|---|---|---|
| -13aa-   | Q | L | HGLELGHS | G | L | Y | A | F |
| -15aa-   | R | L | RSVQLHDS | G | N | Y | C | Y |
| -9 aa-   | V | F | AKITPNNN | G | T | Y | S | C |
| -22aa-   | I | H | PTAELSDS | G | T | Y | A | F |
| -22aa-   | T | N | DHVSFQDA | G | N | Y | T | N |
| -18aa-   | F | H | NAVALGDG | G | H | Y | S | C |
|          |   |   |          |   |   |   | T | R |

FIG. 3A

FIG. 3B

| | | | | | | | | | | |
|---|---|---|---|---|---|---|---|---|---|---|
| hCNTFR | 116 | C | RSNTYPKGSY | S | W | –24aa– | C | –9 aa– | FDEFTI | V |
| hIL6R | 121 | C | FRKSPLSNVV | E | W | –30aa– | C | –10aa– | FQGCGI | L |
| rPRLR | 31 | C | RSPD–KETFT | W | W | –26aa– | C | –10aa– | VDVTYI | V |
| mEPOR | 52 | C | FTQR–LEDLV | F | W | –25aa– | C | –15aa– | IHINEV | V |
| hIL2R | 36 | C | FYNS–RANIS | V | W | –25aa– | C | –11aa– | FKPFEN | L |
| mIL4R | 34 | C | FSDY–IRTST | E | W | –28aa– | C | –11aa– | FSPSGN | V |
| hGM-CSFR | 126 | C | FIYN–ADLMN | T | W | –26aa– | C | –12aa– | LDTKKI | E |

| | | | | | | | | | | |
|---|---|---|---|---|---|---|---|---|---|---|
| KPDP | P | EN | V | VARPVPSNRRLE | T | W | –53aa– | V | AAK----DNEIGT | WS | D | WS |
| QPDP | P | AN | I | TVTAVARNPRWLS | T | W | –50aa– | V | VQLRAQEEFGQGE | WS | E | WS |
| EPEP | P | RN | L | TLEVKQLKDKKTY | – | W | –55aa– | V | QTRCKPDH----GY | WS | R | WS |
| LLDA | P | AG | L | –LARRAEEGSHVV | R | W | –53aa– | V | RARMA–EPSFSGF | WS | A | WS |
| RLMA | P | IS | L | QV–VHVETHRCN– | S | W | –55aa– | V | RVKPL--QGEFTT | WS | P | WS |
| KPLA | P | DN | L | TLHTNVSD–EWL– | T | W | –57aa– | V | RVRS----QILTGT | WS | E | WS |
| RFNP | P | SN | V | TV----RCNTTHCL | R | W | –56aa– | V | KIRAA–D–VRILN | WS | S | WS |

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1591 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 289..1404

( x i ) SEQUENCE DESCRIPTION: SEQ ID NO:1:

```
CCTCGAGATC  CATTGTGCTC  AAAGGGCGGC  GGCAGCGGAG  GCGGCGGCTC  CAGCCGGCGC        60

GGCGCGAGGC  TCGGCGGTGG  GATCCGGCGG  GCGGTGCTAG  CTCCGCGCTC  CCTGCCTCGC       120

TCGCTGCCGG  GGGCGGTCGG  AAGGCGCGGC  GCGAAGCCCG  GGTGGCCCGA  GGGCGCGACT       180

CTAGCCTTGT  CACCTCATCT  TGCCCCCTTG  GTTTTGGAAG  TCCTGAAGAG  TTGGTCTGGA       240

GGAGGAGGAG  GACATTGATG  TGCTTGGTGT  GTGGCCAGTG  GTGAAGAG ATG GCT GCT         297
                                                       Met Ala Ala
                                                        1

CCT GTC CCG TGG GCC TGC TGT GCT GTG CTT GCC GCC GCC GCC GCA GTT            345
Pro Val Pro Trp Ala Cys Cys Ala Val Leu Ala Ala Ala Ala Ala Val
     5                  10                  15

GTC TAC GCC CAG AGA CAC AGT CCA CAG GAG GCA CCC CAT GTG CAG TAC            393
Val Tyr Ala Gln Arg His Ser Pro Gln Glu Ala Pro His Val Gln Tyr
 20                  25                  30                  35

GAG CGC CTG GGC TCT GAC GTG ACA CTG CCA TGT GGG ACA GCA AAC TGG            441
Glu Arg Leu Gly Ser Asp Val Thr Leu Pro Cys Gly Thr Ala Asn Trp
                 40                  45                  50

GAT GCT GCG GTG ACG TGG CGG GTA AAT GGG ACA GAC CTG GCC CCT GAC            489
Asp Ala Ala Val Thr Trp Arg Val Asn Gly Thr Asp Leu Ala Pro Asp
             55                  60                  65

CTG CTC AAC GGC TCT CAG CTG GTG CTC CAT GGC CTG GAA CTG GGC CAC            537
Leu Leu Asn Gly Ser Gln Leu Val Leu His Gly Leu Glu Leu Gly His
         70                  75                  80
```

| | | | | | | | | | | | | | | | | |
|---|---|---|---|---|---|---|---|---|---|---|---|---|---|---|---|---|
| AGT | GGC | CTC | TAC | GCC | TGC | TTC | CAC | CGT | GAC | TCC | TGG | CAC | CTG | CGC | CAC | 585 |
| Ser | Gly | Leu | Tyr | Ala | Cys | Phe | His | Arg | Asp | Ser | Trp | His | Leu | Arg | His | |
| | 85 | | | | 90 | | | | | 95 | | | | | | |
| CAA | GTC | CTG | CTG | CAT | GTG | GGC | TTG | CCG | CCG | CGG | GAG | CCT | GTG | CTC | AGC | 633 |
| Gln | Val | Leu | Leu | His | Val | Gly | Leu | Pro | Pro | Arg | Glu | Pro | Val | Leu | Ser | |
| 100 | | | | | 105 | | | | | 110 | | | | | 115 | |
| TGC | CGC | TCC | AAC | ACT | TAC | CCC | AAG | GGC | TTC | TAC | TGC | AGC | TGG | CAT | CTG | 681 |
| Cys | Arg | Ser | Asn | Thr | Tyr | Pro | Lys | Gly | Phe | Tyr | Cys | Ser | Trp | His | Leu | |
| | | | | 120 | | | | | 125 | | | | | 130 | | |
| CCC | ACC | CCC | ACC | TAC | ATT | CCC | AAC | ACC | TTC | AAT | GTG | ACT | GTG | CTG | CAT | 729 |
| Pro | Thr | Pro | Thr | Tyr | Ile | Pro | Asn | Thr | Phe | Asn | Val | Thr | Val | Leu | His | |
| | | | 135 | | | | | 140 | | | | | 145 | | | |
| GGC | TCC | AAA | ATT | ATG | GTC | TGT | GAG | AAG | GAC | CCA | GCC | CTC | AAG | AAC | CGC | 777 |
| Gly | Ser | Lys | Ile | Met | Val | Cys | Glu | Lys | Asp | Pro | Ala | Leu | Lys | Asn | Arg | |
| | | 150 | | | | | 155 | | | | | 160 | | | | |
| TGC | CAC | ATT | CGC | TAC | ATG | CAC | CTG | TTC | TCC | ACC | ATC | AAG | TAC | AAG | GTC | 825 |
| Cys | His | Ile | Arg | Tyr | Met | His | Leu | Phe | Ser | Thr | Ile | Lys | Tyr | Lys | Val | |
| | 165 | | | | | 170 | | | | | 175 | | | | | |
| TCC | ATA | AGT | GTC | AGC | AAT | GCC | CTG | GGC | CAC | AAT | GCC | ACA | GCT | ATC | ACC | 873 |
| Ser | Ile | Ser | Val | Ser | Asn | Ala | Leu | Gly | His | Asn | Ala | Thr | Ala | Ile | Thr | |
| 180 | | | | | 185 | | | | | 190 | | | | | 195 | |
| TTT | GAC | GAG | TTC | ACC | ATT | GTG | AAG | CCT | GAT | CCT | CCA | GAA | AAT | GTG | GTA | 921 |
| Phe | Asp | Glu | Phe | Thr | Ile | Val | Lys | Pro | Asp | Pro | Pro | Glu | Asn | Val | Val | |
| | | | | 200 | | | | | 205 | | | | | 210 | | |
| GCC | CGG | CCA | GTG | CCC | AGC | AAC | CCT | CGC | CGG | CTG | GAG | GTG | ACG | TGG | CAG | 969 |
| Ala | Arg | Pro | Val | Pro | Ser | Asn | Pro | Arg | Arg | Leu | Glu | Val | Thr | Trp | Gln | |
| | | | 215 | | | | | 220 | | | | | 225 | | | |
| ACC | CCC | TCG | ACC | TGG | CCT | GAC | CCT | GAG | TCT | TTT | CCT | CTC | AAG | TTC | TTT | 1017 |
| Thr | Pro | Ser | Thr | Trp | Pro | Asp | Pro | Glu | Ser | Phe | Pro | Leu | Lys | Phe | Phe | |
| | | 230 | | | | | 235 | | | | | 240 | | | | |
| CTG | CGC | TAC | CGA | CCC | CTC | ATC | CTG | GAC | CAG | TGG | CAG | CAT | GTG | GAG | CTG | 1065 |
| Leu | Arg | Tyr | Arg | Pro | Leu | Ile | Leu | Asp | Gln | Trp | Gln | His | Val | Glu | Leu | |
| | 245 | | | | | 250 | | | | | 255 | | | | | |
| TCC | GAC | GGC | ACA | GCA | CAC | ACC | ATC | ACA | GAT | GCC | TAC | GCC | GGG | AAG | GAG | 1113 |
| Ser | Asp | Gly | Thr | Ala | His | Thr | Ile | Thr | Asp | Ala | Tyr | Ala | Gly | Lys | Glu | |
| 260 | | | | | 265 | | | | | 270 | | | | | 275 | |
| TAC | ATT | ATC | CAG | GTG | GCA | GCC | AAG | GAC | AAT | GAG | ATT | GGG | ACA | TGG | AGT | 1161 |
| Tyr | Ile | Ile | Gln | Val | Ala | Ala | Lys | Asp | Asn | Glu | Ile | Gly | Thr | Trp | Ser | |
| | | | | 280 | | | | | 285 | | | | | 290 | | |
| GAC | TGG | AGC | GTA | GCC | GCC | CAC | GCT | ACG | CCC | TGG | ACT | GAG | GAA | CCG | CGA | 1209 |
| Asp | Trp | Ser | Val | Ala | Ala | His | Ala | Thr | Pro | Trp | Thr | Glu | Glu | Pro | Arg | |
| | | | 295 | | | | | 300 | | | | | 305 | | | |
| CAC | CTC | ACC | ACG | GAG | GCC | CAG | GCT | GCG | GAG | ACC | ACG | ACC | AGC | ACC | ACC | 1257 |
| His | Leu | Thr | Thr | Glu | Ala | Gln | Ala | Ala | Glu | Thr | Thr | Thr | Ser | Thr | Thr | |
| | | 310 | | | | | 315 | | | | | 320 | | | | |
| AGC | TCC | CTG | GCA | CCC | CCA | CCT | ACC | ACG | AAG | ATC | TGT | GAC | CCT | GGG | GAG | 1305 |
| Ser | Ser | Leu | Ala | Pro | Pro | Pro | Thr | Thr | Lys | Ile | Cys | Asp | Pro | Gly | Glu | |
| | 325 | | | | | 330 | | | | | 335 | | | | | |
| CTG | GGC | AGC | GGC | GGG | GGA | CCC | TGC | GCA | CCC | TTC | TTG | GTC | AGC | GTC | CCC | 1353 |
| Leu | Gly | Ser | Gly | Gly | Gly | Pro | Cys | Ala | Pro | Phe | Leu | Val | Ser | Val | Pro | |
| 340 | | | | | 345 | | | | | 350 | | | | | 355 | |
| ATC | ACT | CTG | GCC | CTG | GCT | GCC | GCT | GCC | GCC | ACT | GCC | AGC | AGT | CTC | TTG | 1401 |
| Ile | Thr | Leu | Ala | Leu | Ala | Ala | Ala | Ala | Ala | Thr | Ala | Ser | Ser | Leu | Leu | |
| | | | | 360 | | | | | 365 | | | | | 370 | | |

ATC TGAGCCCGGC ACCCCATGAG GACATGCAGA GCACCTGCAG AGGAGCAGGA    1454
Ile

GGCCGGAGCT GAGCCTGCAG ACCCCGGTTT CTATTTTGCA CACGGGCAGG AGGACCTTTT    1514

GCATTCTCTT CAGACACAAT TTGTGGAGAC CCCGGCGGGC CCGGGCCTGC CGCCCCCCAG    1574

CCCTGCCGCA CCAAGCT    1591

(2) INFORMATION FOR SEQ ID NO:2:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ala Pro Val Pro Trp Ala Cys Cys Ala Val Leu Ala Ala Ala
  1               5                  10                  15

Ala Ala Val Val Tyr Ala Gln Arg His Ser Pro Gln Glu Ala Pro His
             20                  25                  30

Val Gln Tyr Glu Arg Leu Gly Ser Asp Val Thr Leu Pro Cys Gly Thr
         35                  40                  45

Ala Asn Trp Asp Ala Ala Val Thr Trp Arg Val Asn Gly Thr Asp Leu
     50                  55                  60

Ala Pro Asp Leu Leu Asn Gly Ser Gln Leu Val Leu His Gly Leu Glu
 65                  70                  75                  80

Leu Gly His Ser Gly Leu Tyr Ala Cys Phe His Arg Asp Ser Trp His
                 85                  90                  95

Leu Arg His Gln Val Leu Leu His Val Gly Leu Pro Pro Arg Glu Pro
                100                 105                 110

Val Leu Ser Cys Arg Ser Asn Thr Tyr Pro Lys Gly Phe Tyr Cys Ser
            115                 120                 125

Trp His Leu Pro Thr Pro Thr Tyr Ile Pro Asn Thr Phe Asn Val Thr
        130                 135                 140

Val Leu His Gly Ser Lys Ile Met Val Cys Glu Lys Asp Pro Ala Leu
145                 150                 155                 160

Lys Asn Arg Cys His Ile Arg Tyr Met His Leu Phe Ser Thr Ile Lys
                165                 170                 175

Tyr Lys Val Ser Ile Ser Val Ser Asn Ala Leu Gly His Asn Ala Thr
            180                 185                 190

Ala Ile Thr Phe Asp Glu Phe Thr Ile Val Lys Pro Asp Pro Pro Glu
        195                 200                 205

Asn Val Val Ala Arg Pro Val Pro Ser Asn Pro Arg Arg Leu Glu Val
    210                 215                 220

Thr Trp Gln Thr Pro Ser Thr Trp Pro Asp Pro Glu Ser Phe Pro Leu
225                 230                 235                 240

Lys Phe Phe Leu Arg Tyr Arg Pro Leu Ile Leu Asp Gln Trp Gln His
                245                 250                 255

Val Glu Leu Ser Asp Gly Thr Ala His Thr Ile Thr Asp Ala Tyr Ala
            260                 265                 270

Gly Lys Glu Tyr Ile Ile Gln Val Ala Ala Lys Asp Asn Glu Ile Gly
        275                 280                 285

Thr Trp Ser Asp Trp Ser Val Ala Ala His Ala Thr Pro Trp Thr Glu
    290                 295                 300

Glu Pro Arg His Leu Thr Thr Glu Ala Gln Ala Ala Glu Thr Thr Thr
305                 310                 315                 320

Ser Thr Thr Ser Ser Leu Ala Pro Pro Thr Thr Lys Ile Cys Asp
                325                 330                 335

Pro Gly Glu Leu Gly Ser Gly Gly Pro Cys Ala Pro Phe Leu Val
            340                 345                 350

Ser Val Pro Ile Thr Leu Ala Leu Ala Ala Ala Ala Thr Ala Ser
        355                 360                 365

Ser Leu Leu Ile
370
```

( 2 ) INFORMATION FOR SEQ ID NO:3:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Val Thr Leu Thr Cys Xaa Xaa Xaa Xaa Xaa Xaa Xaa Xaa Xaa Val
 1               5                      10                      15

His Trp Val Leu Arg Lys Xaa Xaa Xaa Xaa Xaa Xaa Xaa Xaa Xaa
                20                      25                      30

Xaa Xaa Xaa Xaa Xaa Arg Leu Leu Leu Arg Ser Val Gln Leu His Asp
                35                      40                      45

Ser Gly Asn Tyr Ser Cys Tyr
 50                      55
```

( 2 ) INFORMATION FOR SEQ ID NO:4:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Leu Asn Leu Ser Cys Xaa Xaa Xaa Xaa Xaa Xaa Xaa Xaa Xaa Tyr Ser
 1               5                      10                      15

Trp Arg Ile Xaa Xaa Xaa Xaa Xaa Xaa Xaa Xaa Xaa Val Leu Phe Ile
                20                      25                      30

Ala Lys Ile Thr Pro Asn Asn Asn Gly Thr Tyr Ala Cys Phe
                35                      40                      45
```

( 2 ) INFORMATION FOR SEQ ID NO:5:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Ile Thr Ile Arg Cys Xaa Xaa Xaa Xaa Xaa Xaa Xaa Xaa Xaa Phe Gln
 1               5                      10                      15

Trp Thr Tyr Pro Arg Met Xaa Xaa Xaa Xaa Xaa Xaa Xaa Xaa Xaa Xaa
                20                      25                      30

Xaa Xaa Xaa Xaa Xaa Xaa Xaa Xaa Xaa Xaa Xaa Ile Leu His Ile
                35                      40                      45

Pro Thr Ala Glu Leu Ser Asp Ser Gly Thr Tyr Thr Cys Asn
 50                      55                      60
```

( 2 ) INFORMATION FOR SEQ ID NO:6:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

| Ala | Gln | Ile | Val | Cys | Xaa | Xaa | Xaa | Xaa | Xaa | Xaa | Xaa | Phe | Asp | Val |
|---|---|---|---|---|---|---|---|---|---|---|---|---|---|---|
| 1 | | | | 5 | | | | | 10 | | | | | 15 |

| Ser | Leu | Arg | His | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 20 | | | | | 25 | | | | | 30 | |

| Xaa | Xaa | Xaa | Xaa | Xaa | Xaa | Xaa | Xaa | Xaa | Xaa | Thr | Leu | Asn | Leu | Asp | His |
|---|---|---|---|---|---|---|---|---|---|---|---|---|---|---|---|
| | | 35 | | | | | 40 | | | | | 45 | | | |

| Val | Ser | Phe | Gln | Asp | Ala | Gly | Asn | Tyr | Ser | Cys | Thr |
|---|---|---|---|---|---|---|---|---|---|---|---|
| | 50 | | | | | 55 | | | | | 60 |

( 2 ) INFORMATION FOR SEQ ID NO:7:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

| Val | Thr | Leu | Thr | Cys | Xaa | Xaa | Xaa | Xaa | Xaa | Xaa | Xaa | Phe | Gln | Leu |
|---|---|---|---|---|---|---|---|---|---|---|---|---|---|---|
| 1 | | | | 5 | | | | | 10 | | | | | 15 |

| Arg | Arg | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 20 | | | | | 25 | | | | | 30 | |

| Xaa | Xaa | Xaa | Xaa | Phe | Phe | His | Leu | Asn | Ala | Val | Ala | Leu | Gly | Asp | Gly |
|---|---|---|---|---|---|---|---|---|---|---|---|---|---|---|---|
| | | 35 | | | | | 40 | | | | | 45 | | | |

| Gly | His | Tyr | Thr | Cys | Arg |
|---|---|---|---|---|---|
| | | | | 50 | |

( 2 ) INFORMATION FOR SEQ ID NO:8:

( i ) SEQUENCE CHARACTERISTICS:
        ( A ) LENGTH: 188 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

| Cys | Phe | Arg | Lys | Ser | Pro | Leu | Ser | Asn | Val | Val | Cys | Glu | Trp | Xaa | Xaa |
|---|---|---|---|---|---|---|---|---|---|---|---|---|---|---|---|
| 1 | | | | 5 | | | | | 10 | | | | | 15 | |

| Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|
| | | | 20 | | | | | 25 | | | | | 30 |

| Xaa | Xaa | Xaa | Xaa | Xaa | Xaa | Xaa | Xaa | Xaa | Xaa | Xaa | Xaa | Cys | Xaa | Xaa | Xaa |
|---|---|---|---|---|---|---|---|---|---|---|---|---|---|---|---|
| | | 35 | | | | | 40 | | | | | 45 | | | |

| Xaa | Xaa | Xaa | Xaa | Xaa | Xaa | Xaa | Cys | Xaa | Xaa | Xaa | Xaa | Xaa | Xaa | Xaa |
|---|---|---|---|---|---|---|---|---|---|---|---|---|---|---|
| | 50 | | | | | 55 | | | | | 60 | | | |

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 65 | | | | | 70 | | | | | 75 | | | | | 80 |

| Xaa | Xaa | Xaa | Xaa | Xaa | Xaa | Xaa | Xaa | Phe | Gln | Gly | Cys | Gly | Ile | Leu | Gln |
|---|---|---|---|---|---|---|---|---|---|---|---|---|---|---|---|
| | | | | 85 | | | | | 90 | | | | | 95 | |

| Pro | Asp | Pro | Pro | Ala | Asn | Ile | Thr | Val | Thr | Ala | Val | Ala | Arg | Asn | Pro |
|---|---|---|---|---|---|---|---|---|---|---|---|---|---|---|---|
| | | | 100 | | | | | 105 | | | | | 110 | | |

| Arg | Trp | Leu | Ser | Val | Thr | Trp | Xaa | Xaa | Xaa | Xaa | Xaa | Xaa | Xaa | Xaa |
|---|---|---|---|---|---|---|---|---|---|---|---|---|---|---|
| | | | 115 | | | | | 120 | | | | | 125 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | 130 | | | | | 135 | | | | | 140 | | | |

| Xaa | Xaa | Xaa | Xaa | Xaa | Xaa | Xaa | Xaa | Xaa | Xaa | Xaa | Xaa | Xaa | Xaa | Xaa | Xaa |

|   145         150         155         160 |
| --- |

Xaa Xaa Xaa Xaa Xaa Xaa Xaa Xaa Xaa Val Val Gln Leu Arg Ala Gln
                165                 170             175

Glu Glu Phe Gly Gln Gly Glu Trp Ser Glu Trp Ser
            180                 185

( 2 ) INFORMATION FOR SEQ ID NO:9:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Cys Arg Ser Pro Asp Lys Glu Thr Phe Thr Cys Trp Trp Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Cys Xaa Xaa Xaa Xaa Xaa Xaa Xaa Xaa
                35                  40                  45

Xaa Xaa Cys Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Val Asp Val Thr Tyr Ile Val Glu Pro Glu Pro Pro
                85                  90                  95

Arg Asn Leu Thr Leu Glu Val Lys Gln Leu Lys Asp Lys Lys Thr Tyr
                100                 105                 110

Leu Trp Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Val Gln Thr Arg Cys Lys Pro
                165                 170                 175

Asp His Gly Tyr Trp Ser Arg Trp Ser
            180                 185

( 2 ) INFORMATION FOR SEQ ID NO:10:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Cys Phe Thr Gln Arg Leu Glu Asp Leu Val Cys Phe Trp Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Cys Xaa Xaa Xaa Xaa Xaa Xaa Xaa Xaa Xaa
                35                  40                  45

Xaa Xaa Xaa Xaa Xaa Xaa Cys Xaa Xaa Xaa Xaa Xaa Xaa Xaa Xaa Xaa
        50                  55                  60

```
Xaa Xaa Xaa Xaa Xaa Xaa Xaa Xaa Xaa Xaa Xaa Xaa Xaa Xaa Xaa
 65                      70                      75                      80

Xaa Xaa Xaa Xaa Ile His Ile Asn Glu Val Val Leu Leu Asp Ala Pro
                 85              90                      95

Ala Gly Leu Leu Ala Arg Arg Ala Glu Glu Gly Ser His Val Val Leu
            100             105             110

Arg Trp Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Val Arg Ala Arg Met Ala Glu Pro Ser
                165             170                 175

Phe Ser Gly Phe Trp Ser Ala Trp Ser
            180             185
```

(2) INFORMATION FOR SEQ ID NO:11:

(i) SEQUENCE CHARACTERISTICS:
        (A) LENGTH: 189 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Cys Phe Tyr Asn Ser Arg Ala Asn Ile Ser Cys Val Trp Xaa Xaa Xaa
 1               5                  10                  15

Xaa Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Cys Xaa Xaa Xaa Xaa Xaa Xaa Xaa Xaa
            35              40                      45

Xaa Xaa Cys Xaa Xaa Xaa Xaa Xaa Xaa Xaa Xaa Xaa Xaa Xaa Xaa
        50                  55                      60

Xaa Xaa Xaa Xaa Xaa Xaa Xaa Xaa Xaa Xaa Xaa Xaa Xaa Xaa Xaa
 65                  70                      75                  80

Xaa Xaa Xaa Xaa Xaa Xaa Xaa Xaa Phe Lys Pro Phe Glu Asn Leu Arg
                 85              90                      95

Leu Met Ala Pro Ile Ser Leu Gln Val Val His Val Glu Thr His Arg
            100             105             110

Cys Asn Ile Ser Trp Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Val Arg Val Lys
                165                 170                 175

Pro Leu Gln Gly Glu Phe Thr Thr Trp Ser Pro Trp Ser
            180             185
```

(2) INFORMATION FOR SEQ ID NO:12:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

| Cys | Phe | Ser | Asp | Tyr | Ile | Arg | Thr | Ser | Thr | Cys | Glu | Trp | Xaa | Xaa | Xaa |
|---|---|---|---|---|---|---|---|---|---|---|---|---|---|---|---|
| 1 | | | | 5 | | | | | 10 | | | | | 15 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 20 | | | | | 25 | | | | | 30 | |

| Xaa | Xaa | Xaa | Xaa | Xaa | Xaa | Xaa | Xaa | Xaa | Cys | Xaa | Xaa | Xaa | Xaa | Xaa |
|---|---|---|---|---|---|---|---|---|---|---|---|---|---|---|
| | | | 35 | | | | | 40 | | | | | 45 | |

| Xaa | Xaa | Xaa | Xaa | Xaa | Cys | Xaa | Xaa | Xaa | Xaa | Xaa | Xaa | Xaa | Xaa | Xaa |
|---|---|---|---|---|---|---|---|---|---|---|---|---|---|---|
| | | | 50 | | | 55 | | | | | 60 | | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 65 | | | | | 70 | | | | | 75 | | | | 80 |

| Xaa | Xaa | Phe | Ser | Pro | Ser | Gly | Asn | Val | Lys | Pro | Leu | Ala | Pro | Asp | Asn |
|---|---|---|---|---|---|---|---|---|---|---|---|---|---|---|---|
| | | | | 85 | | | | | 90 | | | | | 95 | |

| Leu | Thr | Leu | His | Thr | Asn | Val | Ser | Asp | Glu | Trp | Leu | Leu | Thr | Trp | Xaa |
|---|---|---|---|---|---|---|---|---|---|---|---|---|---|---|---|
| | | | 100 | | | | 105 | | | | | 110 | | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 115 | | | | | 120 | | | | | 125 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 130 | | | | | 135 | | | | | 140 | |

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 145 | | | | | 150 | | | | | 155 | | | | | 160 |

| Xaa | Xaa | Xaa | Xaa | Xaa | Xaa | Xaa | Xaa | Val | Arg | Val | Arg | Ser | Gln | Ile | Leu |
|---|---|---|---|---|---|---|---|---|---|---|---|---|---|---|---|
| | | | | 165 | | | | | 170 | | | | | 175 | |

| Thr | Gly | Thr | Trp | Ser | Glu | Trp | Ser |
|---|---|---|---|---|---|---|---|
| | | | | 180 | | | |

(2) INFORMATION FOR SEQ ID NO:13:

(i) SEQUENCE CHARACTERISTICS:
 (A) LENGTH: 185 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:13:

| Cys | Phe | Ile | Tyr | Asn | Ala | Asp | Leu | Met | Asn | Cys | Thr | Trp | Xaa | Xaa | Xaa |
|---|---|---|---|---|---|---|---|---|---|---|---|---|---|---|---|
| 1 | | | | 5 | | | | | 10 | | | | | 15 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 20 | | | | | 25 | | | | | 30 | |

| Xaa | Xaa | Xaa | Xaa | Xaa | Xaa | Xaa | Cys | Xaa | Xaa | Xaa | Xaa | Xaa | Xaa | Xaa |
|---|---|---|---|---|---|---|---|---|---|---|---|---|---|---|
| | | | 35 | | | | | 40 | | | | | 45 | |

| Xaa | Xaa | Xaa | Xaa | Cys | Xaa | Xaa | Xaa | Xaa | Xaa | Xaa | Xaa | Xaa | Xaa |
|---|---|---|---|---|---|---|---|---|---|---|---|---|---|
| | | | 50 | | | 55 | | | | | 60 | | |

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 65 | | | | | 70 | | | | | 75 | | | | | 80 |

| Xaa | Xaa | Xaa | Xaa | Leu | Asp | Thr | Lys | Lys | Ile | Glu | Arg | Phe | Asn | Pro | Pro |
|---|---|---|---|---|---|---|---|---|---|---|---|---|---|---|---|
| | | | | 85 | | | | | 90 | | | | | 95 | |

| Ser | Asn | Val | Thr | Val | Arg | Cys | Asn | Thr | Thr | His | Cys | Leu | Val | Arg | Trp |
|---|---|---|---|---|---|---|---|---|---|---|---|---|---|---|---|
| | | | 100 | | | | | 105 | | | | | 110 | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 115 | | | | | 120 | | | | | 125 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 130 | | | | | 135 | | | | | 140 | |

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 145 | | | | | 150 | | | | | 155 | | | | | 160 |

```
Xaa Xaa Xaa Xaa Xaa Xaa Xaa Xaa Val Lys Ile Arg Ala Ala Asp Val
                165                 170                 175
Arg Ile Leu Asn Trp Ser Ser Trp Ser
            180             185
```

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GACTCGAGTC GACATCGGAG GCTGATGGGA TGCC      34

( 2 ) INFORMATION FOR SEQ ID NO:15:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CTAAAGACTC CTCCTAGACA TCGCCGGCGT ATCG      34

CILIARY NEUROTROPHIC FACTOR RECEPTOR

This patent application is a continuation-in-part of U.S. patent application Ser. No. 07/532,285, filed Jun. 1, 1990, now abandoned, which is incorporated by reference herein in its entirety.

TABLE OF CONTENTS

1. Introduction
2. Background Of The Invention
   2.1. Ciliary Neurotrophic Factor
   2.2. Functional Properties Of Ciliary Neurotrophic Factor
   2.3. Growth Factor Receptors
3. Summary Of The Invention
4. Description Of The Figures
5. Detailed Description Of The Invention
   5.1. Cloning Of The Ciliary Neurotrophic Factor Receptor
   5.2. Nucleic Acid Encoding Ciliary Neurotrophic Factor Receptor
   5.3. Ciliary Neurotrophic Factor Receptor Peptides
   5.4. Expression of Ciliary Neurotrophic Factor Receptor
   5.5. Identification Of Molecules Related To The Ciliary Neurotrophic Factor Receptor
   5.6. Utility Of The Invention
      5.6.1. Assay Systems
      5.6.2. Experimental Model Systems
         5.6.2.1. Models For Increased CNTF Activity
         5.6.2.2. Models For Decreased CNTF Activity
      5.6.3. Diagnostic Applications
      5.6.4. Therapeutic Applications
6. Example: Expression Cloning Of The Ciliary Neurotrophic Factor Receptor
   6.1. Materials And Methods
      6.1.1. Construction Of A CNTF-Receptor Expression Library
      6.1.2. "Panning" Method
      6.1.3. Identification Of Clones Containing The Ciliary Neurotrophic Factor Receptor Gene
      6.1.4. Direct $^{125}$I-hCNTF Binding Assay.
      6.1.5. Fluorescence Activated Cell-Sorting Analysis
      6.1.6. Iodination Of hCNTF
      6.1.7. Sequencing of CNTFR
      6.1.8. Indirect $^{125}$ Goat Anti-Mouse Antibody Binding Assay
   6.2. Results And Discussion
      6.2.1. Restriction Analysis
      6.2.2. In Vitro Transcription And Translation
      6.2.3. Binding Analysis With CNTF
      6.2.4. Sequence Of CNTFR And Homology To Other Growth Factor Receptors
Example: Tissue Localization Of Message For CNTFR
   7.1. Materials And Methods
      7.1.1. CNTFR Probe Preparation
      7.1.2. RNA Preparation And Northern Blots
   7.2. Results
8. Example: Evidence That The CNTF Receptor Is Linked To The Cell Surface Via A Glycosyl-Phosphatidylinositol (GPI) Linkage
   8.1. Materials and Methods
   8.2. Results And Discussion
9. Deposit of Microorganisms

1. INTRODUCTION

The present invention relates to the ciliary neurotrophic factor receptor (CNTFR), and provides for CNTF receptor encoding nucleic acid and amino acid sequences. It also relates to (i) assay systems for detecting CNTF activity; (ii) experimental model systems for studying the physiological role of CNTF; (ii) diagnostic techniques for identifying CNTF-related neurologic conditions; (iv) therapeutic techniques for the treatment of CNTF-related neurologic conditions, and (v) methods for identifying molecules homologous to CNTFR.

2. BACKGROUND OF THE INVENTION

2.1. CILIARY NEUROTROPHIC FACTOR

Ciliary neurotrophic factor (CNTF) is a protein that is specifically required for the survival of embryonic chick ciliary ganglion neurons in vitro (Manthorpe et al., 1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervate the ciliary muscle and sphincter pupillae.

Ciliary ganglion neurons have been found to be among the neuronal populations which exhibit defined periods of cell death. In the chick ciliary ganglion, half of the neurons present at embryonic day 8 (E8) have been observed to die before E14 (Landmesser and Pilar, 1974, J. Physiol. 241:737–749). During this same time period, ciliary ganglion neurons are forming connections with their target tissues, namely, the ciliary body and the chorioid coat of the eye. Landmesser and Pilar (1974, J. Physiol. 241:751–736) observed that removal of an eye prior to the period of cell death results in the complete loss of ciliary ganglion neurons in the ipsilateral ganglion. Conversely, Narayanan and Narayanan (1978, J. Embryol. Ex. Morphol. 44:53–70) observed that, by implanting an additional eye primordium and thereby increasing the amount of available target tissue, ciliary ganglion neuronal cell death may be decreased. These results are consistent with the existence of a target derived neurotrophic factor which acts upon ciliary ganglion neurons.

In culture, ciliary ganglion (CG) neurons have been found to require a factor or factors for survival. Ciliary neurotrophic factor(s) (CNTF) activity has been identified in chick muscle cell conditioned media (Helfand et al., 1976, Dev. Biol. 50-541-547; Helfand et al., 1978, Exp. Cell Res. 113-39-45; Bennett and Nurcome, 1979, Brain Res. 173:543–548, Nishi and Berg, 1979, Nature 277-232-234; Varon et al., 1979, Brain Res. 173:29–45), in muscle extracts (McLennan and Hendry, 1978, Neurosci. Lett. 10:269–273); in chick embryo extract (Varon et al., 1979, Brain Res. 173:29–45; Tuttle et al., 1980, Brain Res. 183:161–180), and in medium conditioned by heart cells (for discussion, see also Adler et al., 1979, Science 204:1434–1436 and Barbin et al., 1984, J. Neurochem. 43:1468–1478).

Adler et al. (1979, Science 204:1434–1436) used an assay system based on microwell cultures of CG neurons to demonstrate that a very rich source of CNTF was found in the intraocular target tissues the CG neurons innervate. Out of 8000 trophic units (TU) present in a twelve-day embryo, 2500 TU were found present in eye tissue; activity appeared to be localized in a fraction containing the ciliary body and choroid coat.

Subsequently, Barbin et al. (1984, *J. Neurochem.* 43:1468-1478) reported a procedure for enriching CNTF from chick embryo eye tissue. CNTF activity was also found to be associated with non-CG tissues, including rat sciatic nerve (Williams et al., 1984, *Int. J. Develop. Neurosci* 218:460-470). Manthorpe et al. (1986, *Brain Res.* 367:282-286) reported partial purification of mammalian CNTF activity from extracts of adult rat sciatic nerve using a fractionation procedure similar to that employed for isolating CNTF activity from chick eye. In addition, Watters and Hendry (1987*J. Neurochem.* 49:705-713) described a method for enriching CNTF activity approximately 20,000-fold from bovine cardiac tissue under non-denaturing conditions using heparin-affinity chromatography. CNTF activity has also been identified in damaged brain tissue (Manthorpe et al., 1983, *Brain Res.* 267:47-56; Nieto-Sampedro et al., 1983, *J. Neurosci.* 3:2219-2229).

Carnow et al. (1985, *J. Neurosci.* 5: 1965-1971) and Rudge et al., (1987, *Develop. Brain Res.* 32:103-110) describe methods for identifying CNTF-like activity from Western blots of tissue extracts and then identifying protein bands containing CNTF activity by inoculating the nitrocellulose strips in a culture dish with CG neurons and identifying areas of cell survival using vital dyes. Using this method, Carnow et al. (1985, *J. Neurosci.* 5:1965-1971) observed that adult rat sciatic nerve and brain-derived CNTF activities appear to exhibit a different size (24 kD) than chick CNTF (20.4 kD).

Recently, CNTF has been cloned and synthesized in bacterial expression systems, as described in U.S. patent application Ser. No. 07/570,651, entitled "*Ciliary Neurotrophic Factor,*" filed Aug. 20, 1990 by Sendtner et al. incorporated by reference in its entirety herein. Using recombinant probes, CNTF-mRNA in tissues of adult rat appeared to be about 1.2 kb in size. Rat brain CNTF was cloned and found to be encoded by a mRNA having a short 5' untranslated region of 77 bp and an open reading frame of 600 bp, predicting a protein of about 200 amino acids (Stockli et al., 1989, *Nature* 342:920-923). Human CNTF was also cloned and sequenced (U.S. patent application Ser. No. 07/570,651, entitled "*Ciliary Neurotrophic Factor,*" filed Aug. 20, 1990 by Sendtner et al.); its coding sequences were substantially conserved relative to rat sequences, whereas noncoding sequences were less conserved.

2.2. FUNCTIONAL PROPERTIES OF CILIARY NEUROTROPHIC FACTOR

A number of biological effects have been ascribed to CNTF. As discussed above, CNTF was originally described as an activity which supported the survival of neurons of the E8 chick ciliary ganglion, a component of the parasympathetic nervous system. A description of other biological properties of preparations known to contain CNTF activity follows:

Saadat et al. (1989, *J. Cell Biol.* 108:1807-1816) observed that their most highly purified preparation of rat sciatic nerve CNTF induced cholinergic differentiation of rat sympathetic neurons in culture. Also, Hoffman (1988, *J. Neurochem.* 51:109-113) found that CNTF activity derived from chick eye increased the level of choline-O-acetyltransferase activity in retinal monolayer cultures.

Hughes et al. (1988, *Nature* 335:70-73) studied a population of bipotential glial progenitor cells in cultures derived from the perinatal rat optic nerve and brain; these progenitor cells have been shown to give rise to, first, oligodendrocytes and then, to type 2 astrocytes. Under the culture conditions used, oligodendrocyte differentiation appeared to occur directly from an oligodendrocyte-type 2-astrocyte (O-2A) progenitor cell, whereas type 2 astrocyte differentiation appears to require the presence of an inducing protein similar or identical to CNTF (see also Anderson, 1989, *Trends Neurosci.* 12:83-85).

Heymanns and Unsicker (1979, *Proc. Natl. Acad. Sci. U.S.A.* 4:7758-7762) observed that high-speed supernatants of neuroblastoma cell extracts produced effects similar to those associated with CNTF activity from chick eye or rat sciatic nerve; the presence of a protein similar but not identical to CNTF (by molecular weight) was indicated.

Ebendal (1987, *J. Neurosci. Res.* 17:19-24) looked for CNTF-like activity in a variety of rat and chicken tissues. He observed CNTF-like activity among a fairly wide range of rat, but not in chicken tissues; rat liver, spleen T cells, and submandibular gland cells were found to be associated with low levels of CG survival promoting activity, whereas heart, brain, and skeletal muscle tissues were associated with higher survival promoting activity. Among tissues tested the highest CNTF-like activity was observed to be associated with rat kidney.

While the above studies have shown that many tissue and cell extracts contain activities which support the survival of neuronal populations which are also responsive to CNTF, (i.e. they support the survival of E8 chick ciliary ganglion neurons in a tissue culture bioassay), it cannot be assumed that a single or identical protein is responsible for these activities. As shown for the family of fibroblast growth factors (FGFs) (Dionne et al., 1990, *EMBO J.* 9:2685-2692), for example, a number of distinct polypeptides or proteins possess identical biological activity in a single bioassay.

The neuronal specificity of chick eye and rat sciatic nerve CNTF were initially found to have some overlap with neuronal populations responsive to NGF. Although CNTF was observed to have some overlapping neuronal specificity with NGF, distinguishing characteristics between them became most apparent in studies of the roles of CNTF and NGF in populations of developing neurons (Skaper and Varon, 1986, *Brain Res.* 389:39-46). In addition to their differing roles in development, CNTF may also be distinguished from NGF by molecular weight, isoelectric point, inability to be inactivated by antibodies to NGF, and by CNTF's ability to support the in vitro survival of CGF neurons (Barbin et al., 1984, *J. Neurochem.* 43:1468-1478). Lin et al. (1989), *Science* 246:1023-1026 have reported that CNTF is without sequence homology to any previously reported proteins. Sendtner et al. (U.S. patent application Ser. No. 07/570,651, entitled "*Ciliary Neurotrophic Factor,*" filed Aug. 20, 1990) observed that recombinant CNTF promoted survival of mediodorsal and ventral spinal cord neurons, and also that purified rat sciatic nerve CNTF appeared to prevent cell death of motorneurons in lesioned facial nerve (VIIth cranial nerve) of newborn rat (Sendtner et al., 1990, *Nature* 345:440-441).

The cloning and expression of CNTF using recombinant DNA technology has led to the discovery of a number of CNTF activities.

2.3. GROWTH FACTOR RECEPTORS

A number of receptors which mediate binding and response to protein factors have been characterized and molecularly cloned over the last few years, including receptors for insulin, for platelet derived growth factor, for epidermal growth factor and its relatives, for the fibroblast growth factors, and for various interleukins and hematopoietic growth factors. Recent data reveal that certain receptors can bind to multiple (related) growth factors, while in other cases the same factor can act on multiple (related) receptors (e.g. Lupu et al., 1990, *Science* 249:1552–1555; Dionne et al., 1990, *EMBO J.* 9:2685–2692; Miki et al., 1991, *Science* 251:72–75). Most receptors that bind protein factors can broadly be characterized as having extracellular portions responsible for specifically binding the factor, transmembrane regions which span the membrane, and intracellular domains that are often involved in initiating signal transduction upon binding of the protein factor to the receptor's extracellular portion. Interestingly, although many receptors are comprised of a single polypeptide chain, other receptors apparently require (at least) two separate subunits in order to bind to their factor with high-affinity and to allow functional response following binding (e.g. Hempstead et al., 1989, *Science* 243:373–375; Hibi et al., 1990, *Cell* 63:1149–1157). The extracellular and intracellular portions of a given receptor often share common structural motifs with the corresponding regions of other receptors, suggesting evolutionary and functional relationships between different receptors. These relationships can often be quite distant and may simply reflect the repeated use of certain general domain structures. For example, a variety of different receptors that bind unrelated factors make use of "immunoglobulin" domains in their extracellular portions, while other receptors utilize "cytokine receptor" domains in their factor-binding regions (e.g. Akira et al., 1990, *The FASEB J.* 4:2860–2867). A large number of receptors with distinct extracellular binding domains (which thus bind different factors) contain related intracytoplasmic domains encoding tyrosine-specific protein kinases that are activated in response to factor binding (e.g. Ullrich and Schlessinger, 1990, *Cell* 61:203–212). The mechanisms by which factor-binding "activates" the signal transduction process is poorly understood, even in the case of receptor tyrosine kinases. For other receptors, in which the intracellular domain encodes a domain of unknown function or in which the binding component associates with a second protein of unknown function (e.g. Hibi et al., 1990, *Cell* 63:1149–1157), activation of signal transduction remains even more mysterious.

3. SUMMARY OF THE INVENTION

The present invention relates to CNTF receptor (CNTFR) genes and proteins. It is based, in part, on the cloning and characterization of the human CNTFR gene and its expression in transfected COS cells.

The present invention provides for nucleic acid sequences which encode the CNTFR, as well as fragments derived therefrom. It also provides for substantially purified CNTFR protein, and for peptide fragments thereof.

In a further aspect of the invention, CNTFR probes, including nucleic acid as well as antibody probes, may be used to identify CNTFR-related molecules. For example, the present invention provides for such molecules which form a complex with CNTFR and thereby participate in CNTFR function. As another example, the present invention provides for receptor molecules which are homologous or cross-reactive antigenically, but not identical to CNTFR. These particular embodiments are based on the discovery that the CNTFR bears homology to other biologically relevant molecules, including, most particularly, the IL-6 receptor, but also the PDGF receptor, the CSF-1 receptor, the prolactin receptor, the IL-2 and IL-4 receptors, the GM-CSF granulocyte macrophage colony stimulation factor receptor, pregnancy-specific alpha 1-beta glycoprotein, and carcinoembryonic antigen, a tumor marker.

The present invention also provides for assay systems for detecting CNTF activity, comprising cells which express high levels of CNTFR, and which are therefore extremely sensitive to even very low concentrations of CNTF or CNTF-like molecules.

In addition, the present invention provides for experimental model systems for studying the physiological role of CNTF. Such systems include animal models, such as (i) animals exposed to circulating CNTFR peptides which compete with cellular receptor for CNTF binding and thereby produce a CNTF-depleted condition, (ii) animals immunized with CNTFR; (iii) transgenic animals which express high levels of CNTFR and therefore are hypersensitive to CNTF; and (iv) animals derived using embryonic stem cell technology in which the endogenous CNTFR genes were deleted from the genome.

In yet further embodiments of the invention, CNTFR probes may be used to identify cells and tissues which are responsive to CNTF in normal or diseased states. For example, a patient suffering from a CNTF-related disorder may exhibit an aberrancy of CNTFR expression.

In addition, the CNTFR genes and proteins of the invention may be used therapeutically. For example, and not by way of limitation, a circulating CNTFR may be used to deplete CNTF levels in areas of trauma to the central nervous system. Alternatively, a recombinant CNTFR gene may be inserted in tissues which would benefit from increased sensitivity to CNTF, such as motorneurons in patients suffering from amyotrophic lateral sclerosis.

4. DESCRIPTION OF THE FIGURES

FIGS. 1A–1D. Schematic diagram of expression cloning using tagged ligand binding strategy. B(i-ii). Secondary iodinated antibody assay showed that in contrast to COS cells transfected with the original cDNA library, many COS cells transfected with DNA obtained after one round of panning expressed CNTF-binding sites (radioautograph done on 60 mm plate of transfected COS cells; each black dot represents a single transfected COS cell expressing a CNTF-binding site). C(i-ii). The same assay as described in (B), but where COS cells had been transfected with a non-CNTFR encoding plasmid (negative clone) or a CNTFR encoding plasmid (positive clone). Only small sections of each plate are shown. D(i-ii). Results of fluorescence activated cell sorting (FACS) analysis of COS cells transfected with the negative clone or the positive clone of (C).

FIGS. 2A–2D. Nucleic acid sequence of CNTFR-encoding cDNA (SEQ ID NO:1) and deduced amino acid sequence (SEQ ID NO:2).

FIGS. 3A–3B. Alignment of the human CNTFR showing homologies in the immunoglobulin-like domain (SEQ ID NO:2 through NO:7) and the cytokine receptor-like domain (SEQ ID NO:2 and NO:9 through NO:13). Numbers on the left indicate the amino acid number starting from the first methionine. Identical residues and conserved substitutions are marked by solid boxes. Gaps are introduced to maximize homology. hCNTFR IgG-like domain=SEQ ID NO.2, Cytokine-like domain=SEQ ID NO. 2. IL-6=interleukin 6 (IgG-like domain=SEQ ID NO:3, cytokine-like domain=SEQ ID NO. 8); CEA=carcinoembryonic antigen (IgG-like domain=SEQ ID NO:4), PDGF=platelet derived growth factor (IgG-like domain=SEQ ID NO:5), CSF-1=colony stimulating factor 1 (IgG-like domain=SEQ ID NO:6); alpha 1-$\beta$ GP=alpha 1 $\beta$ glycoprotein (IgG-like domain=SEQ ID NO:7), PRL=prolactin (cytokine domain=SEQ ID NO:9), EPO=erythropoietin (cytokine domain=SEQ ID NO:10); IL-2=interleukin 2 (cytokine domain=SEQ ID NO:11); IL-4=interleukin 4 (cytokine domain=SEQ ID NO:12), GM-CSF=granulocyte macrophage colony stimulating factor (cytokine domain=SEQ ID NO:13).

Figure 4:
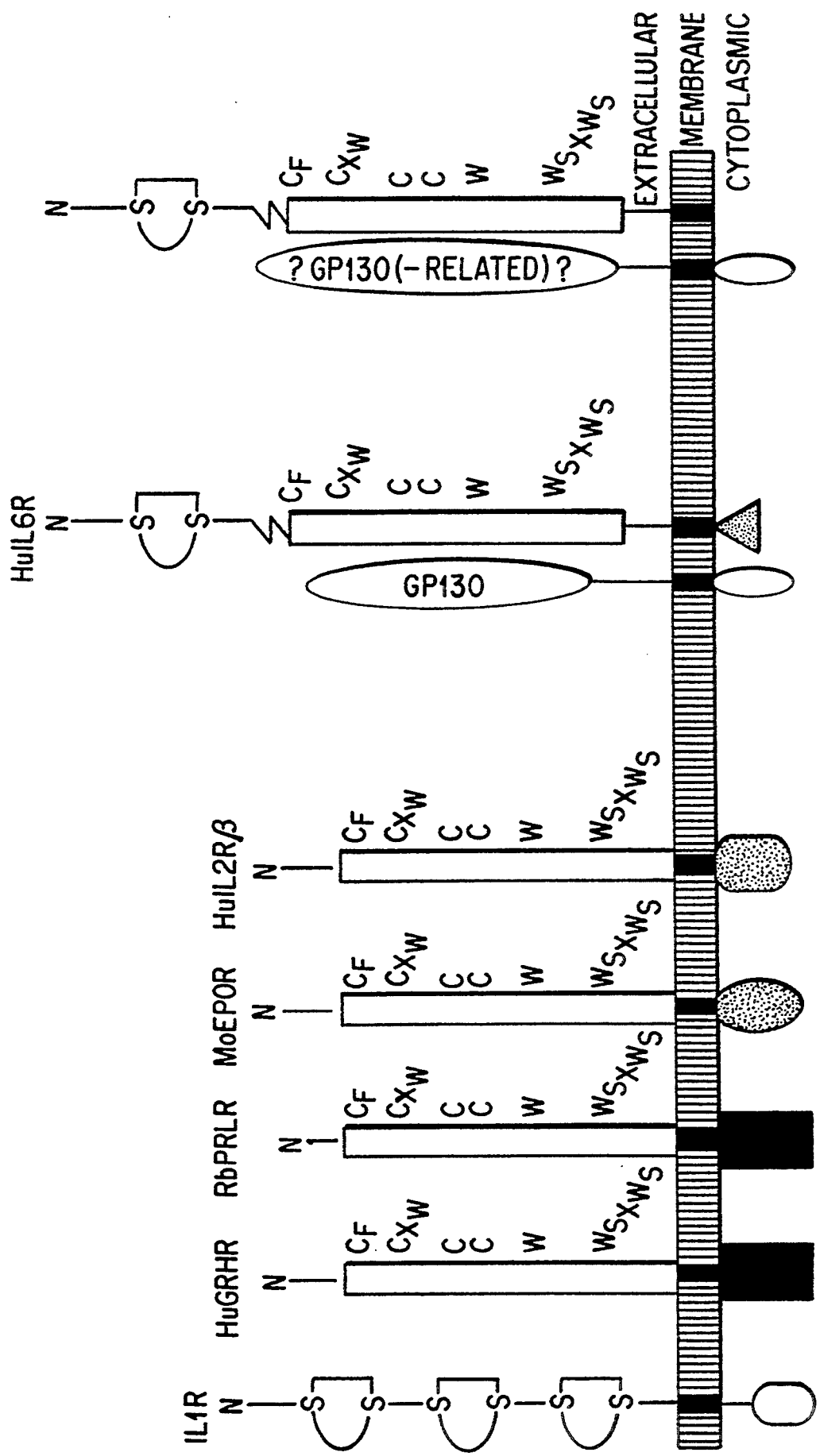

FIG. 4. Structural relationships between the CNTFR and other related receptors. The human IL-6 receptor and CNTFR have an immunoglobulin domain fused to the N-terminus of the proposed factor binding domain. A short acidic tether (zig zag line) connects the globular immunoglobulin and proposed factor binding domain. A proposed protein similar to gp130 is shown in association with the CNTFR, as discussed in the text. HuGRHR-human growth hormone receptor; RbPRLR-rabbit prolactin receptor; MoEPOR-mouse erythropoietin receptor; HuIL2R$\beta$-human interleukin-2 receptor $\beta$-chain; HuIL6R-human interleukin 6 receptor; HuCNTFR-human ciliary derived neurotrophic factor receptor; C-cysteine; X-unknown amino acid; W-tryptophan; S-serine; F-phenylalanine.

Figure 5:
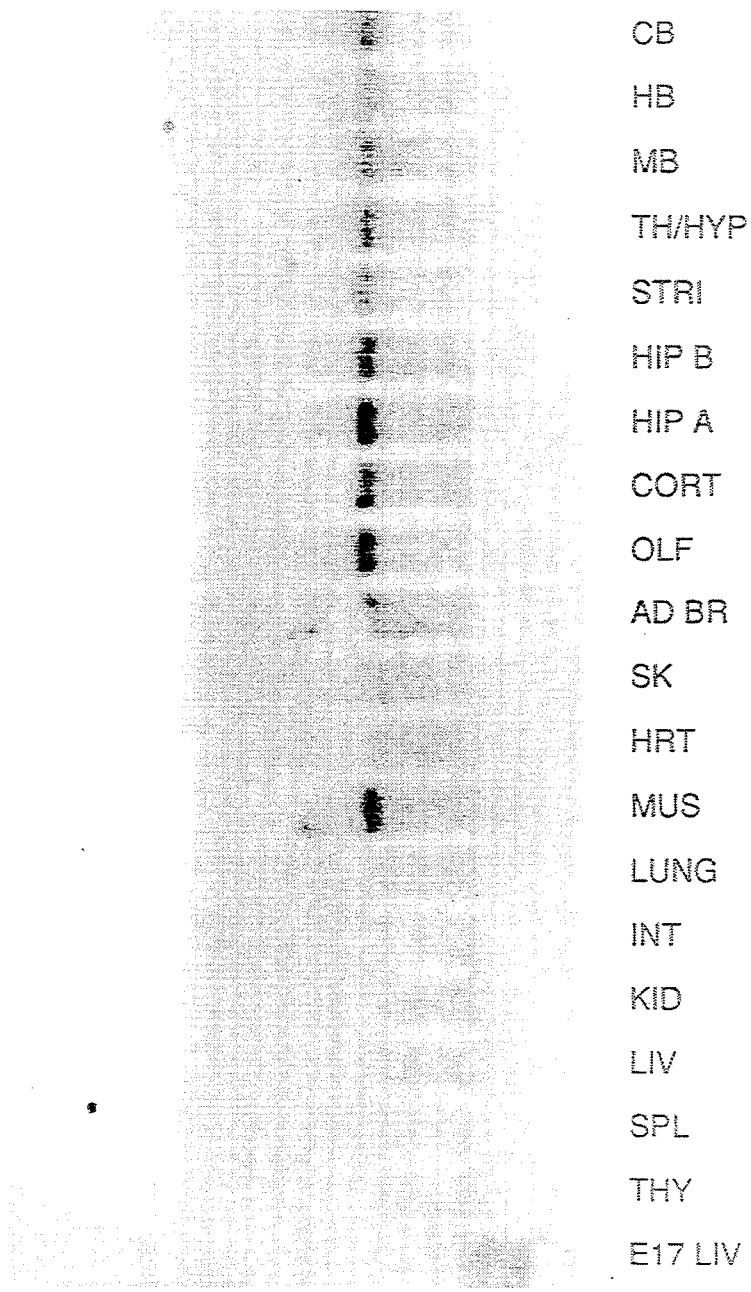

FIG. 5. Tissue localization of CNTFR message. RNA was prepared from the indicated tissues of rat as described in section 8.1. DNA fragments of CNTFR were derived from expression constructs containing these genes in pCMX as described in section 8.1. Tissues: cerebellum (CB); hindbrain (HB); midbrain (MB); thalamus (TH/HYP); striatum (STRI); hippocampus B (HIP B); hippocampus A (HIP A); cortex (CORT); olfactory bulb (OLF); adult brain (AD BR); skin (SK);heart (HRT); muscle (MUS), lung (LUNG); intestine (INT); kidney (KID); liver (LIV); spleen (SPL); thymus (THY); E17 liver (E17 LIV).

Figure 6:
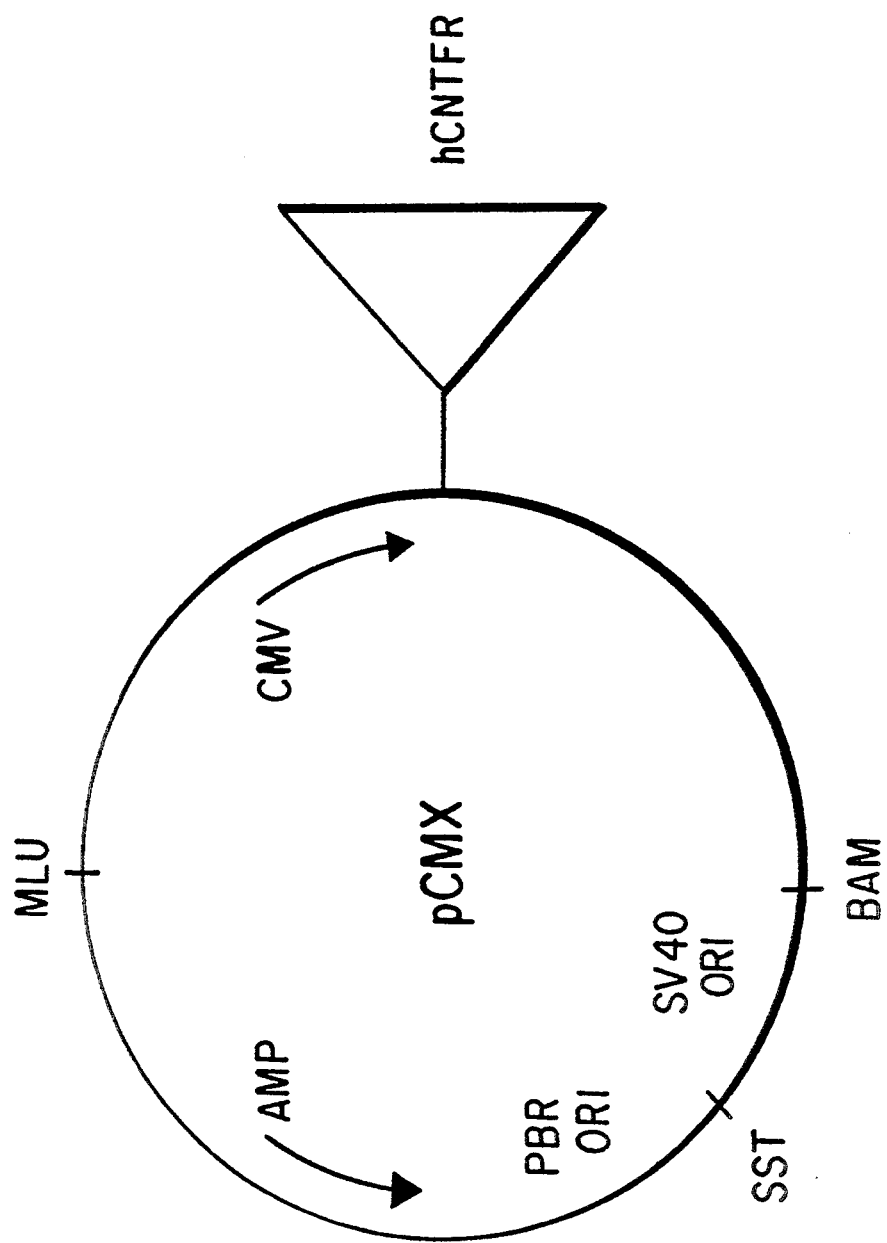

FIG. 6. pCMX with hCNTF-R gene insert. Construction of pCMX in copending application.

5. DETAILED DESCRIPTION OF THE INVENTION

For purposes of clarity of disclosure, and not by way of limitation, the detailed description of the invention will be divided into the following subsections:
(i) cloning of the CNTF receptor;
(ii) nucleic acid encoding the CNTF receptor;
(iii) CNTFR peptides;
(iv) expression of CNTF receptor;
(v) identification of molecules related to the CNTF receptor; and
(vi) utility of the invention.

5.1. CLONING OF THE CILIARY NEUROTROPHIC FACTOR RECEPTOR

The present invention enables the cloning of the CNTF receptor (CNTFR) by providing a method for selecting target cells which express CNTFR. By providing a means of enriching for CNTFR encoding sequences, the present invention enables the purification of CNTFR protein and the direct cloning of CNTFR-encoding DNA.

For example, CNTFR-bearing target cells may be selected, and CNTFR protein may be purified using methods known to one skilled in the art for the purification of a receptor molecule. For example, and not by way of limitation, CNTF or CNTF attached to a detectable molecule, as described in section 5.6.3, infra, in which the tag may be, for example, a radiolabel, antigenic determinant, or antibody, to name a few, (CNTF/tag) may be reversibly crosslinked to target cells, and membrane associated proteins from said target cells may be subjected to purification methods. Such purification methods may include SDS-PAGE, followed by detection of the position of CNTF or CNTF/tag in the gel; for example, radiolabeled CNTF could be used, and, crosslinked to its receptor, may be visualized in the gel by autoradiography. Alternatively, anti-CNTF or anti-tag antibody could be used in the Western blot technique to identify the position of the CNTF/receptor complex in such gels. Preparative gel electrophoresis could be used to isolate sufficient amounts of protein to enable amino acid sequencing of peptide fragments of the receptor, or to enable production of anti-CNTFR antibody which could be used to purify CNTFR molecules from target cell extracts. Amino acid sequence obtained from purified CNTFR may be used to design degenerate oligonucleotide probes which may be used to identify CNTFR encoding cloned nucleic acid in a genomic DNA library or, preferably, in a cDNA library constructed from CNTFR producing target cells.

Alternatively, the CNTFR may be cloned by subtractive hybridization methods, in which mRNA may be prepared from target cells which express CNTFR, and then non-CNTFR encoding sequences may be subtracted by hybridizing the mRNA (or cDNA produced therefrom) with mRNA or cDNA derived from cells such as neuronal cells which do not express the CNTFR. The nucleic acid remaining after subtraction is likely to be enriched in CNTFR-encoding sequences.

Nucleic acid prepared, preferably, from target cells enriched in CNTFR encoding sequences due to endogenous expression of CNTFR and/or due to subtraction techniques discussed supra, may also be used in expression cloning techniques to directly clone the CNTFR. For example, and not by way of limitation, total genomic DNA from target cells which express CNTFR may be prepared and then transfected into a cell line which does not express CNTFR and which is preferably derived from a different species from the target cell species (for example, DNA from a human CNTFR-encoding cell may be transfected into a mouse cell, such as an L cell). Although a relatively small number of transfected cells may express CNTFR, such cells may be identified by rosetting techniques or immunofluorescence techniques as described in section 5.6.3, infra and may be isolated, for example, by fluorescence-activated cell sorting or using antibody-coupled magnetic beads or "panning" techniques, known to one skilled in the art. The CNTFR encoding DNA may be cloned from receptor-producing transfectants by producing a genomic library from the transfectants and then isolating and propagating clones that contain either sequences conforming to CNTFR amino acid sequence or sequences homologous to species specific genetic elements; for example, human DNA may be identified via Alu repeated sequences, which are distributed at high frequency throughout the human genome. For example, and not by way of limitation, cultured non-human cells comprising transfected human DNA encoding the CNTFR and which express human CNTFR may be selected, propagated, and then genomic DNA prepared from these cells may be used to transfect cultured non-human cells, and CNTFR expressing cells may be selected. This process may be repeated; its purpose is to decrease, by each transfection step, the amount of human DNA present in CNTFR encoding cells. Accordingly, when the genomic DNA of transfected, human CNTFR expressing cells is cloned to generate a library, clones which include human DNA (and are identified, for example, by screening for distinctly human sequence elements) are more likely to comprise CNTFR-encoding sequences when repeated transfections have been performed.

RNA from a CNTFR expressing cell line or tissue source, or a cDNA expression library obtained from such a source may be introduced in pools into Xenopus oocytes by direct injection; oocytes injected with pools encoding the CNTFR may be identified by assaying for functional responses (e.g. ion fluxes) that may be induced by exposing such oocytes to CNTF, or alternatively by detecting the presence of CNTF-binding sites on the surface of such injected oocytes. Repetitively dividing positive pools into smaller and smaller pools may lead to the identification of individual clones encoding the CNTFR.

Alternatively, a cDNA expression library may be derived from CNTFR bearing target cells and then utilized in transient expression assays. In a preferred embodiment of the invention, said expression library may incorporate the SV40 origin of replication and transient expression assays may be performed using COS cells. CNTFR-expressing transfectants may be identified as set forth above, and CNTFR encoding DNA may be retrieved using standard methods. The nucleic acid sequence encoding the CNTFR may then be propagated and/or utilized in expression systems using methods substantially as set forth for nucleic acid encoding CNTF, as described in U.S. patent application Ser. No. 07/570,651, entitled "Ciliary Neurotrophic Factor," filed Aug. 20, 1990 by Sendtner et al.

In a specific embodiment of the invention, exemplified in Section 6, infra, (and see FIG. 1) expression cloning of the CNTFR may be performed as follows. A cDNA library may be prepared from a cell line or tissue which expresses CNTFR such as SH-SY5Y, such that the cDNA is inserted into an expression vector. This library may then be transfected into a suitable cell line, such as COS M5 cells, using, for example, a DEAE/chloroquine transfection protocol. Several days after transfection, the cells may be detached from their culture dishes and subjected to the Aruffo/Seed panning procedure (Seed and Aruffo, 1987, Proc. Natl. Acad. Sci. U.S.A. 84:365–3369), with the following modifications:
 (i) instead of incubating the transfected cells with anti-receptor antibodies, the cells may be incubated first with tagged CNTF (for example, CNTF myc) on ice for about 30 minutes, centrifuged through phosphate buffered saline (PBS)/2% Ficoll to remove excess ligand, and then incubated with anti-tag antibody (for example, the anti-myc antibody 9E10) for about 30 minutes on ice.
 (ii) the cells may then be spun through PBS/2% Ficoll and then "panned" on plates coated with antibody that recognizes the anti-tag antibody (for example, if the anti-tag antibody is 9E10, anti-mouse antibody.

Then, after washing nonadherent cells from the plates, Hirt supernatants may be prepared from the adherent cells, and plasmid DNA may be precipitated in the presence of about 10–20µg of tRNA. The resulting plasmid DNA may then be introduced into suitable bacteria (for example DH10 B bacteria) by standard techniques, including, but not limited to, electroporation. The cultures grown from transformed bacteria may then be used to prepare plasmid DNA for another round of eukaryotic transfection and panning. After this second transfection, panning and plasmid DNA preparation and transformation, the bacterial transformants may be plated out on selective media, individual colonies may be picked and used for the preparation of plasmid DNA, and DNA prepared from a number of such clones may be used individually for COS cell transfection. Alternatively, more rounds of enrichment may be necessary before individual colonies are tested. Resulting COS cells expressing CNTF binding sites may be identified by a number of techniques, including, but not limited to, indirect binding assays using radioactively labeled or fluorescently labeled indicator antibodies. An example of a CNTFR-encoding nucleic acid is comprised in pCMX-hCNTFR (I2), FIG. 6, which has been deposited with the NRLL and assigned accession number B-18789, and which is described in copending United States patent application Serial No. entitled "Mammalian Expression Vector" by Davis and Yancopoulos. Clones identified in this manner may then be analyzed by restriction fragment mapping and nucleic acid sequencing using standard techniques. Fragments of the CNTFR-encoding cDNA may then be used to identify genomic DNA sequences which comprise the CNTFR gene, for example, from a genomic DNA library using standard hybridization techniques.

Once obtained, a CNTFR gene may be cloned or subcloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or Bluescript® (Stratagene) plasmid derivatives. Recombinant molecules can be introduced into host cells via transformation, transfection, infection, electroporation, etc.

The CNTFR gene may be inserted into a cloning vector which can be used to transform, transfect, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. It may prove advantageous to incorporate restriction endonuclease cleavage sites into the oligonucleotide primers used in polymerase chain reaction to facilitate insertion into vectors. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and CNTFR gene may be modified by homopolymeric tailing.

In specific embodiments, transformation of host cells with recombinant DNA molecules that incorporate an isolated CNTFR gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

5.2. NUCLEIC ACID ENCODING CILIARY NEUROTROPHIC FACTOR RECEPTOR

Using the methods detailed supra and in Example Section 6, infra, the following nucleic acid sequence (SEQ ID NO:1) was determined, and the corresponding amino acid sequence (SEQ ID NO:2) deduced. The sequence of the human CNTFR is depicted in FIGS. 2-2D (SEQ ID NO:1). This sequence, its functional equivalent, or fragments of this sequence at least 6 nucleotides in length may be used in accordance with the invention. Additionally, the invention relates to CNTFR genes isolated from porcine, ovine, bovine, feline, avian, equine, or canine, as well as primate sources and any other species in which CNTF activity exists. Subsequences comprising hybridizable portions of the CNTFR sequence have use, e.g., in nucleic acid hybridization assays, Southern and Northern blot analyses, etc.

For example, the nucleic acid sequence depicted in FIGS. 2A-2D (SEQ ID NO:1) can be altered by mutations such as substitutions, additions or deletions that provide for sequences encoding functionally equivalent molecules. According to the present invention, a molecule is functionally equivalent or active compared with a molecule having the sequence depicted in FIGS. 2A-2D (SEQ ID NO:2) if it has the ability to bind CNTF, but it does not necessarily bind CNTF with an affinity comparable to that of natural CNTFR. Due to the degeneracy of nucleotide coding sequences, other DNA sequences which encode substantially the same amino acid sequence as depicted in FIGS. 2A-2D (SEQ ID NO:2) may be used in the practice of the present invention. These include but are not limited to nucleotide sequences comprising all or portions of the CNTFR gene depicted in FIGS. 2A-2D (SEQ ID NO:1) which is altered by the substitution of different codons that encode a functionally equivalent amino acid residue within the sequence, thus producing a silent change.

In addition, the recombinant CNTFR-encoding nucleic acid sequences of the invention may be engineered so as to modify processing or expression of CNTFR. For example, and not by way of limitation, the CNTFR gene may be combined with a promoter sequence and/or a ribosome binding site, or a signal sequence may be inserted upstream of CNTFR encoding sequences to permit secretion of CNTFR and thereby facilitate harvesting or bioavailability.

Additionally, a given CNTFR can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TAB ® linkers (Pharmacia), etc.

5.3. CILIARY NEUROTROPHIC FACTOR RECEPTOR PEPTIDES

The invention also provides for CNTFR proteins, fragments and derivatives thereof, having the amino acid sequence set forth in FIGS. 2A-2D (SEQ ID NO:2) or its functional equivalents and for proteins homologous to such protein, such homology being of at least about 30 percent. The invention also provides fragments or derivatives of CNTFR proteins which comprise at least six amino acids, comprise an antigenic determinant(s), or which are functionally active. The CNTFR protein having the amino acid sequence depicted in FIGS. 2A-2D (SEQ ID NO:2) has a molecular weight of approximately 42 kd.

CNTFR proteins, or fragments or derivatives thereof, of the invention include, but are not limited to, those containing, as a primary amino acid sequence, all or part of the amino acid sequence substantially as depicted in FIGS. 2A-2D (SEQ ID NO. 2) including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are CNTFR proteins or fragments or derivatives thereof which are differentially modified during or after translation, e.g., by phosphorylation, glycosylation, cross-linking, acylation, proteolytic cleavage, linkage to an antibody molecule, membrane molecule or other ligand, (Ferguson et al., 1988, Ann. Rev. Biochem. 57:285-320).

The CNTFR peptides of the invention may be prepared by recombinant nucleic acid expression techniques or by chemical synthesis using standard peptide synthesis techniques.

5.4. EXPRESSION OF CILIARY NEUROTROPHIC FACTOR RECEPTOR

In order to express recombinant CNTFR, the nucleotide sequence coding for a CNTFR protein, or a portion thereof, can be inserted into an appropriate expression vector, i.e., a vector which contains the necessary elements for the transcription and translation of the inserted protein-coding sequence. The necessary transcription and translation signals can also be supplied by the native CNTFR gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

In a preferred specific embodiment of the invention, the CNTFR gene may be comprised in the pCMX expression vector, as deposited with the ATCC and assigned accession no. B 18789.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding CNTFR protein or peptide fragment may be regulated by a second nucleic acid sequence so that CNTFR protein or peptide is expressed in a host transformed with the recombinant DNA molecule. For example, expression of CNTFR may be controlled by any promoter/enhancer element known in the art. Promoters which may be used to control CNTFR expression include, but are not limited to, the SV40 early promoter region (Bernoist and Chambon, 1981, *Nature* 290:304–310), the CMV promoter, the promoter contained in the 3' long terminal repeat of Rous sarcoma virus (Yamamoto, et al., 1980, *Cell* 22:787–797), the herpes thymidine kinase promoter (Wagner et al., 1981, *Proc. Natl. Acad. Sci. U.S.A.* 78:144–1445), the regulatory sequences of the metallothionine gene (Brinster et al., 1982, *Nature* 296:39–42); prokaryotic expression vectors such as the β-lactamase promoter (Villa-Kamaroff, et al., 1978, *Proc. Natl. Acad. Sci. U.S.A.* 75:3727–3731), or the tac promoter (DeBoer, et al., 1983, *Proc. Natl. Acad. Sci. U.S.A.* 80:21–25), see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, Cold Spring Harbor *Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, *Science* 235:53–58); alpha 1-antitrypsin gene control region which is active in the liver (Kelsey et al, 1987, *Genes and Devel.* 1:161–171), beta-globin gene control region which is active in myeloid cells (Mogram et al., 1985, *Nature* 315:338–340; Kollias et al., 1986, *Cell* 46:89–94); myelin basic protein gene control region which is active in oligodendrocyte cells in the brain (Readhead et al., 1987, *Cell* 48:703–712); myosin light chain-2 gene control region which is active in skeletal muscle (Sani, 1985, *Nature* 314:283–286), and gonadotropic releasing hormone gene control region which is active in the hypothalamus (Mason et al., 1986, *Science* 234:1372–1378).

Expression vectors containing CNTFR gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted CNTFR gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the CNTFR gene is inserted within the marker gene sequence of the vector, recombinants containing the CNTFR insert can be identified by the absence of the marker gene function. In the third approach, recombinant expression vectors can be identified by assaying the foreign gene product expressed by the recombinant. Such assays can be based, for example, on the physical or functional properties of the CNTFR gene product, for example, by binding of the receptor to CNTF or to an antibody which directly recognizes the CNTFR.

In an additional embodiment, cells which do not normally express CNTFR may be transfected with recombinant-CNTFR encoding nucleic acid and then tested for the expression of functional CNTFR by exposing the transfectants to CNTF and then testing for an increase in cAMP levels.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered CNTFR protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast may be used to produce a glycosylated product. Expression in mammalian cells can be used to ensure "native" glycosylation of the heterologous CNTFR protein. Furthermore, different vector/host expression systems may effect processing reactions such as proteolytic cleavages to different extents.

Once a recombinant which expresses the CNTFR gene is identified, the gene product should be analyzed. This can be achieved by assays based on the physical or functional properties of the product.

Once the CNTFR protein is identified, it may be isolated and purified by standard methods including chromatography (e.g., ion exchange, affinity, and sizing column chromatography), centrifugation, differential solubility, or by any other standard technique for the purification of proteins. In particular, CNTFR protein may be isolated by binding to an affinity column comprising CNTF bound to a stationary support.

Nucleic acid sequences complementary to DNA or RNA sequences encoding CNTFR or a functionally active portion thereof are also provided. In a particular aspect, antisense oligonucleotides can be synthesized, which are complementary to at least a portion of CNTFR mRNA.

5.5. IDENTIFICATION OF MOLECULES RELATED TO THE CILIARY NEUROTROPHIC FACTOR RECEPTOR

Multiple receptor-factor systems have been defined in which the same factor can bind to multiple receptors (see supra). As this may be the case for CNTF, the present invention allows for the identification of any additional CNTF receptors by the identical scheme used to obtain the CNTFR described here, except for the source of RNA used to prepare the cDNA expression library. A source may be chosen that would be likely to be expressing a distinct CNTF receptor; sources may be evaluated for the presence of CNTF-binding not attributable to the CNTFR (genetic probes and antibody reagents generated from the CNTFR sequence may be used to compare the protein responsible for CNTF binding in cell lines or tissue sources with the CNTF described here). In addition, because receptors are known which bind to more than one related factor (see supra), identification of the CNTFR should allow identification of any additional native ligands which bind this receptor.

In a further aspect of the invention, the CNTFR sequence may be used in the identification of CNTFR-related molecules. The CNTFR contains motifs which are shared with a variety of other receptors. The extracellular portion of the CNTFR contains both an "immunoglobulin" domain at its N-terminus, as well as a "cytokine receptor" domain which is separated from the "immunoglobulin" domain by a short hinge region. Although many receptors have homology to either the "immunoglobulin" or "cytokine receptor" domains, only one receptor—the IL-6 receptor—shares the same particular arrangement of these domains with the CNTFR. The IL-6 receptor is thus the protein most related to the CNTFR. Interestingly, the IL-6 receptor is also similar to the CNTFR in that it has a very short intracytoplasmic domain which is apparently not required for initiating responses upon IL-6 binding (Hibi et al., 1990, Cell 63:1149-1157). Recently, a novel signal transducer for the IL-6 receptor, termed gp 130, was molecularly cloned. This transducer does not bind IL-6 by itself, but it does confer high affinity binding to the IL-6 receptor and it is required to transduce the IL-6 signal (Hibi et al., 1990, Cell 63:1149-1157). Cloning of the CNTFR reveals that it shares important features with the IL-6 receptor that are not found in other known receptors, thus defining a new family of receptors. Homologies between these first two members of this receptor family, as defined by the present invention, may be used to identify additional related receptors by using DNA or antibody probes corresponding to homologous regions, or by using a polymerase chain reaction strategy together with degenerate oligonucleotides corresponding to shared regions of amino acid homology (e.g. Maisonpierre et al., 1990, Science 247:1146-1451). The present invention may also be used for the testing of whether the CNTFR utilizes the same signal transducer as the IL-6 receptor, or whether it utilizes a related molecule. Finally, the identification of CNTFR-related receptors should aid in the identification of novel ligands that would bind to these receptors.

According to the present invention, by screening a DNA library (comprising genomic DNA or, preferably, cDNA) with oligonucleotides corresponding to CNTFR sequence derived either from protein sequence data or from the nucleic acid sequence set forth in FIGS. 2A-2B (SEQ ID NO:1 and NO:2), clones may be identified which encode new members of the family described above. By decreasing the stringency of hybridization, the chances of identifying somewhat divergent members of the family may be increased. It may also be desirable to use sequences substantially shared by members of the family which have been sequenced; such highly conserved regions may be particularly useful in identifying additional members of the family. Library screening may be performed using, for example, the hybridization technique of Benton and Davis (1977, Science 196:180) or Grunstein and Hogness (1975, Proc. Natl. Acad. Sci. U.S.A. 72:3961-3965). Clones identified by hybridization may then be further analyzed, and new family members may be identified by restriction fragment mapping and sequencing techniques according to methods well known in the art.

It may be desirable to utilize polymerase chain reaction (PCR) technology (Saiki et al., 1985, Science 230:1350-1354) to identify additional members of the CNTFR superfamily. For example, sense and antisense primers corresponding to known CNTFR sequence may be used in PCR, preferably using cDNA as template. It may be desirable to design these primers such that they include restriction enzyme cleavage sites which may facilitate the insertion of the products of PCR into appropriate cloning vectors. The products of PCR may be inserted into suitable vectors and the resulting clones may then be screened for new family members. Such screening may be performed using standard techniques, including hybridization analysis using probes corresponding to known sequence. For example, a series of probes representing different regions of a characterized CNTFR protein may be hybridized at low stringency to duplicate filters carrying DNA from clones generated using PCR, as outlined above. It may be observed that various clones may hybridize to some probes, but not others. New family members may also be identified by increasing the stringency of the hybridization conditions, wherein new members not identical to probes derived from known members would hybridize less strongly at higher stringency. Alternatively, new family members may be identified by restriction mapping or sequencing analysis using standard techniques to reveal differences in restriction maps or sequences relative to known family members.

In additional embodiments, the present invention provides for molecules which form a complex with CNTFR and thereby may participate in CNTFR function. For example, it has been found that CNTFR does not, by sequence analysis, appear to possess a cytoplasmic domain; it may, in fact, be joined to a membrane through GPI linkage glycosyl-phosphatidylinositol (reviewed in Ferguson et al., 1988, *Ann. Rev. Biochem.* 57:285–320). This suggests that at least one other molecule forms an association with CNTFR to participate in signal transduction across the cell membrane. Such a molecule may be, for example, a protein such as GP130 that is found associated with IL-6R (Taga et al., 1989, *Cell* 58:573–581); this is particularly likely in light of the homology between CNTFR and the IL-6 receptor. Molecules which are associated with CNTFR at the cell membrane may be isolated and identified by any method known in the art, including but not limited to chemical cross-linkage, coprecipitation with anti-CNTFR antibody, or via a CNTF/tag, and/or by protein or lipid purification techniques.

Further, the present invention provides for molecules other than CNTF which may bind to CNTFR. Such molecules are defined as molecules which compete with CNTF, including other normal ligands, for CNTFR binding, and include peptides, peptide derivatives and non-peptide (e.g. peptidomimetic) compounds.

5.6. UTILITY OF THE INVENTION

5.6.1. ASSAY SYSTEMS

The present invention provides for assay systems in which CNTF activity or activities similar to CNTF activity resulting from exposure to a peptide or non-peptide compound may be detected by measuring a physiological response to CNTF in a cell or cell line responsive to CNTF which expresses the CNTFR molecules of the invention. A physiological response may comprise any of the biological effects of CNTF, including but not limited to, those described in Section 2.2, supra, as well as the transcriptional activation of certain nucleic acid sequences (e.g. promoter/enhancer elements as well as structural genes), CNTF-related processing, translation, or phosphorylation, the induction of secondary processes in response to processes directly or indirectly induced by CNTF, and morphological changes, such as neurite sprouting, or the ability to support the survival of cells such as ciliary ganglion cells, motorneurons, Purkinje cells, or hippocampal neurons, to name but a few.

In a preferred specific embodiment of the invention, the functional interaction between CNTF and the CNTFR may be observed by detecting an increase in the production of "immediate early" primary response genes activated in response to many growth factor-stimulated transmembrane signals, including, but not limited to, c-fos and c-jun. For example, the activation of immediate early genes may be detected by Northern blot analysis of immediate early gene mRNA levels. In a preferred embodiment of the invention, c-fos or c-jun mRNA levels may be determined by Northern blot analysis of mRNA prepared from target cells incubated with CNTF, wherein CNTF activity is evidenced by an increase in levels of c-fos or c-jun. Of note, in particular embodiments of the invention, once target cells have been produced that contain recombinant CNTFR-encoding nucleic acid or selected by virtue of binding to CNTF, it may be desirable to ensure that the target cells respond characteristically to CNTF or compounds with CNTF-like activity. In the context of the present invention, the term CNTF-like activity is construed to mean biological activity which is similar but may or may not be identical to that of CNTF; such activities would include but are not limited to those described in Section 2.2, supra or the activation of particular immediate early promoters such as the fos or jun promoters.

The present invention provides for the development of novel assay systems which may be utilized in the screening of compounds for CNTF- or CNTF-like activity. Target cells which bind to CNTF may be produced by transfection with CNTFR-encoding nucleic acid or may be identified and segregated by, for example, fluorescent-activated cell sorting, sedimentation of rosettes, or limiting dilution as described in Section 5.6.3, infra.

Once target cell lines are produced or identified, it may be desirable to select for cells which are exceptionally sensitive to CNTF. Such target cells may bear a greater number of CNTFRs; target cells bearing a relative abundance of CNTFRs could be identified by selecting target cells which bind to high levels of CNTF, for example cells which when incubated with CNTF/tag and subjected to immunofluorescence assay produce a relatively higher degree of fluorescence. Alternatively, cells which are exceptionally sensitive to CNTF may exhibit a relatively strong biological response, such as a sharp increase in immediate early gene products such as c-fos or c-jun, in response to CNTF binding. By developing assay systems using target cells which are extremely sensitive to CNTF, the present invention provides for methods of screening for CNTF or CNTF-like activity which are capable of detecting low levels of CNTF activity.

In particular, using recombinant DNA techniques, the present invention provides for CNTF target cells which are engineered to be highly sensitive to CNTF. For example, the CNTF-receptor gene, cloned according to the methods set forth in Section 5.1, may be inserted into cells which are naturally CNTF responsive such that the recombinant CNTFR gene is expressed at high levels and the resulting engineered target cells express a high number of CNTFRs on their cell surface.

Alternatively, or additionally, the target cells may be engineered to comprise a recombinant gene which is expressed at high levels in response to CNTF/receptor binding. Such a recombinant gene may preferably be associated with a readily detectable product. For example, and not by way of limitation, transcriptional control regions (i.e. promoter/enhancer regions) from an immediate early gene may be used to control the expression of a reporter gene in a construct which may be introduced into target cells. The immediate early gene/reporter gene construct, when expressed at high levels in target cells by virtue of a strong promoter/enhancer or high copy number, may be used to produce an amplified response to CNTFR binding. For example, and not by way of limitation, a CNTF-responsive promoter (such as the c-fos or c-jun promoter) may be used to control the expression of detectable reporter genes including $\beta$-galactosidase, growth hormone, chloramphenicol acetyl transferase, neomycin phosphotransferase, luciferase, or $\beta$-glucuronidase. Detection of the products of these reporter genes, well known to one skilled in the art, may serve as a sensitive indicator for CNTF or CNTF-like activity of pharmaceutical compounds.

The CNTFR-encoding or reporter gene constructs discussed above may be inserted into target cells using any method known in the art, including but not limited to transfection, electroporation, calcium phosphate/DEAE dextran methods, and cell gun, as well as the production of transgenic animals bearing the above-mentioned constructs as transgenes, and from which CNTF target cells may be selected using the methods discussed Assay systems of the present invention enable the efficient screening of pharmaceutical compounds for utility in the treatment of CNTF-associated diseases. For example, and not by way of limitation, it may be desirable to screen a pharmaceutical agent for CNTF activity and therapeutic efficacy in cerebellar degeneration. In a specific embodiment of the invention, Purkinje cells responsive to CNTF may be identified and isolated, and then cultured in microwells in a multiwell culture plate. Culture medium with added test agent, or added CNTF, in numerous dilutions may be added to the wells, together with suitable controls. The cells may then be examined for improved survival, neurite sprouting, and so forth, and the activity of test agent and CNTF, as well as their relative activities, may be determined. As another example, motorneuron lesions have been shown to respond favorably to CNTF (Sendtner et al., 1990, Nature 345:440). It may, therefore, be desirable to identify CNTF-like compounds which can, like CNTF, prevent motorneuron cell death following axotomy. CNTF responsive motorneurons could be utilized in assay systems to identify compounds useful in treating motorneuron diseases. Considering that CNTF has been found to be effective in preventing motorneuron cell death following axotomy, which clearly is an extremely important observation when contemplating treatments for spinal cord injuries, amyotrophic lateral sclerosis, and diabetic neuropathy, in designing drugs which would be effective in treating these disorders, including drugs which may be required to pass the blood brain barrier, it is essential to have access to a reliable and sensitive screening system such as the methods the present invention provide. For another example, if a particular disease is found to be associated with a defective CNTF response in a particular tissue, a rational treatment for the disease would be supplying the patient with exogenous CNTF. However, it may be desirable to develop molecules which have a longer half-life than endogenous CNTF, or which act as CNTF agonists, or which are targeted to a particular tissue. Accordingly, the methods of the invention can be used to produce efficient and sensitive screening systems which can be used to identify molecules with the desired properties. Similar assay systems could be used to identify CNTF antagonists.

5.6.2. EXPERIMENTAL MODEL SYSTEMS

The present invention also provides for experimental model systems for studying the physiological role of CNTF. In these model systems, CNTFR protein, peptide fragment, or a derivative thereof, may be either supplied to the system or produced within the system. Such model systems could be used to study the effects of CNTF excess or CNTF depletion. The experimental model systems may be used to study the effects of increased or decreased response to CNTF in cell or tissue cultures, in whole animals, in particular cells or tissues within whole animals or tissue culture systems, or over specified time intervals (including during embryogenesis) in embodiments in which CNTFR expression is controlled by an inducible or developmentally regulated promoter. In particular embodiments of the invention, the CMV promoter may be used to control expression of CNTFR in transgenic animals. The term "transgenic animals," as used herein, refers to non-human transgenic animals, including transgenic mosaics, which carry a transgene in some or all of their cells, which include any non-human species, and which are produced by any method known in the art, including, but not limited to microinjection, cell fusion, transfection, electroporation, etc. For example, the animals may be produced by a microinjection of zygotes method such as that set forth in "Brinster et al, 1989, Proc. Natl. Acad. Sci. U.S.A. 82:4438–4442.

The present invention also provides for model systems for autoimmune disease in which an autoimmune response is directed toward CNTFR. Such models comprise animals which have been immunized with immunogenic amounts of CNTFR and preferably found to produce anti-CNTFR antibodies and/or cell-mediated immunity. To produce such a model system, it may be desirable to administer the CNTFR in conjunction with an immune adjuvant, such as Bacille Calmette Guerin (BCG).

5.6.2.1. MODELS FOR INCREASED CNTF ACTIVITY

For example, and not by way of limitation, an experimental model system may be created which may be used to study the effects of excess CNTF activity. In such a system, the response to CNTF may be increased by engineering an increased number of CNTFRs on cells of the model system relative to cells which have not been so engineered. It may be preferable to provide an increased number of CNTFRs selectively on cells which normally express CNTFRs.

Cells may be engineered to produce increased numbers of CNTFR by infection with a virus which carries a CNTFR gene of the invention. Alternatively, the CNTFR gene may be provided to the cells by transfection.

If the model system is an animal, a recombinant CNTFR gene may be introduced into the cells of the animal by infection with a virus which carries the CNTFR gene. Alternatively, a transgenic animal may be created which carries the CNTFR gene as a transgene.

In order to ensure expression of CNTFR, the CNTFR gene should be placed under the control of a suitable promoter sequence. It may be desirable to put the CNTFR gene under the control of a constitutive and/or tissue specific promoter, including but not limited to the CNS neuron specific enolase, neurofilament, and tyrosine hydroxylase promoter, an inducible promoter, such as the metallothionein promoter, the UV activated promoter in the human immunodeficiency virus long terminal repeat (Valeri et al., 1988, Nature 333:78–81), or the CMV promoter (as contained in pCMX, infra) or a developmentally regulated promoter.

By increasing the number of cellular CNTFRs, the response to endogenous CNTF may be increased. If the model system contains little or no CNTF, CNTF may be added to the system. It may also be desirable to add additional CNTF to the model system in order to evaluate the effects of excess CNTF activity. Over expressing CNTF (or secreted CNTF) may be the preferable method for studying the effects of elevated levels of CNTF on cells already expressing CNTFR. More preferably would be to express CNTFR in all cells (general expression) and determine which cells are then endowed with functional responsiveness to CNTF, thus allowing the potential identification of a second receptor component, if one exists.

5.6.2.2. MODELS FOR DECREASED CNTF ACTIVITY

Alternatively, as an example, and not by way of limitation, an experimental model system may be created which may be used to study the effects of diminished CNTF activity. This system may permit identification of processes or neurons which require CNTF, and which may represent potential therapeutic targets. In such a system, the response to CNTF may be decreased by providing recombinant CNTFRs which are not associated with a cell surface or which are engineered so as to be ineffective in transducing a response to CNTF.

For example, CNTFR protein, peptide, or derivative may be supplied to the system such that the supplied receptor may compete with endogenous CNTFR for CNTF binding, thereby diminishing the response to CNTF. The CNTFR may be a cell free receptor which is either added to the system or produced by the system. For example, a CNTFR protein which lacks the transmembrane domain may be produced by cells within the system, such as an anchorless CNTFR that may be secreted from the producing cell. Alternatively, CNTFR protein, peptide or derivative may be added to an extracellular space within the system.

In additional embodiments of the invention, a recombinant CNTFR gene may be used to inactivate or "knock out" the endogenous gene by homologous recombination, and thereby create a CNTFR deficient cell, tissue, or animal. For example, and not by way of limitation, a recombinant CNTFR gene may be engineered to contain an insertional mutation, for example the neo gene, which inactivates CNTFR. Such a construct, under the control of a suitable promoter, may be introduced into a cell, such as an embryonic stem cell, by a technique such as transfection, transduction, injection, etc. Cells containing the construct may then be selected by G418 resistance. Cells which lack an intact CNTFR gene may then be identified, e.g. by Southern blotting or Northern blotting or assay of expression. Cells lacking an intact CNTFR gene may then be fused to early embryo cells to generate transgenic animals deficient in CNTFR. A comparison of such an animal with an animal not expressing endogenous CNTF would reveal that either the two phenotypes match completely or that they do not, implying the presence of additional CNTF-like factors or receptors.

Such an animal may be used to define specific neuronal populations, or any other in vivo processes, normally dependent upon CNTF. Thus, these populations or processes may be expected to be effected if the animal did not express CNTFR and therefore could not respond to CNTF.

Alternatively, a recombinant CNTFR protein, peptide, or derivative which competes with endogenous receptor for CNTF may be expressed on the surface of cells within the system, but may be engineered so as to fail to transduce a response to CNTF binding.

The recombinant CNTFR proteins, peptides or derivatives described above may bind to CNTF with an affinity that is similar to or different from the affinity of endogenous CNTFR to CNTF. To more effectively diminish the response to CNTF, the CNTFR protein, peptide, or derivative may desirably bind to CNTF with a greater affinity than that exhibited by the native receptor.

If the CNTFR protein, peptide, or derivative is produced within the model system, nucleic acid encoding the CNTFR protein, peptide, or derivative may be supplied to the system by infection, transduction, transfection, etc. or as a transgene. As discussed supra, the CNTFR gene may be placed under the control of a suitable promoter, which may be, for example, a tissue-specific promoter or an inducible promoter or developmentally regulated promoter.

In a specific embodiment of the invention the endogenous CNTFR gene of a cell may be replaced by a mutant CNTFR gene by homologous recombination.

In a further embodiment of the invention, CNTFR expression may be reduced by providing CNTFR expressing cells with an amount of CNTFR anti-sense RNA or DNA effective to reduce expression of CNTFR protein.

5.6.3. DIAGNOSTIC APPLICATIONS

According to the present invention, CNTFR probes may be used to identify cells and tissues which are responsive to CNTF in normal or diseased states. The present invention provides for methods for identifying cells which are responsive to CNTF comprising detecting CNTFR expression in such cells. CNTFR expression may be evidenced by transcription of CNTFR mRNA or production of CNTFR protein. CNTFR expression may be detected using probes which identify CNTFR nucleic acid or protein.

One variety of probe which may be used to detect CNTFR expression is a nucleic acid probe, which may be used to detect CNTFR-encoding RNA by any method known in the art, including, but not limited to, in situ hybridization, Northern blot analysis, or PCR related techniques.

Another variety of probe which may be used is tagged CNTF, as set forth in U.S. Ser. No. 07/532,285, the complete text of which is incorporated by reference herein.

According to the present invention, the term "tagged" CNTF should be construed to mean a CNTF molecule which is attached to a second detectable compound (the "tag"). The detectable compound may comprise radioisotope, a fluorescent moiety, or a ligand capable of binding to a receptor, or a substance which may be detected colorimetrically or which has catalytic activity. In preferred embodiments, the tag may comprise an antigenic determinant such that antibody is capable of binding to the tag. In alternative embodiments the tag itself may be an antibody; in a specific embodiment of the invention the tag is monoclonal antibody RP3-17. It is desirable that the tag not interfere with the biological activity of CNTF and that the methods of detection of the tag would not substantially interfere with the binding of CNTF to its receptor.

The tag may be attached to CNTF using any method known in the art. In preferred embodiments of the invention, the tag is covalently linked to CNTF but in some cases it may be desirable that the tag be attached by noncovalent forces (for example, if the tag comprises an immunoglobulin molecule).

The tag may be of any molecular size suitable for preserving its detector function without substantially altering the biological activity of the attached CNTF. If the tag is to provide an antigenic determinant, it may be desirable that it comprise at least about 5-15 amino acids.

For purposes of illustration, and not by way of limitation, in one preferred specific method of the invention, CNTF may be tagged using a "patch" polymerase chain reaction in which recombinant neurotrophic factor (CNTF) is engineered to carry at its C-terminal end ten amino acids corresponding to a known antigenic determinant. For example, and not by way of limitation, this antigenic determinant may correspond to a defined epitope of the human c-myc proto-oncogene protein.

For example, and not by way of limitation, the "patch" PCR method may be used to attach the ten amino acid myc tag as follows (the present invention provides for any amino acid tag attached by analogous methods). A 5′ PCR primer corresponding to an CNTF sequence upstream of a unique restriction enzyme cleavage site in a bacterial expression construct may be utilized in PCR reaction with a "patch" primer comprising nucleic acid sequence corresponding to 3′ terminal CNTF sequence and nucleic acid sequence encoding the peptide tag, using cDNA from CNTF-responsive cells as template.

The PCR reaction should also comprise a 3′ primer corresponding to the patch primer sequence and including nucleic acid sequence which incorporates unique restriction endonuclease cleavage sites. In preferred embodiments, the 5′ and 3′ primers may be used in excess of patch primer, such that PCR amplification between 5′ and patch primers may cease after a few PCR cycles whereas amplification between the 5′ and 3′ primers may initiate and continue to produce a high yield of full length CNTF/tag sequence. The "patch" technique overcomes the need for long primers whose synthesis may be difficult and time consuming. The amplified CNTF/tag product may be gel purified, digested with restriction enzymes which cleave at the sites engineered into the termini of the product, and then subcloned into the corresponding restriction sites of an expression vector. For example, to produce CNTF-myc tag, the following primers may be used: 5′ primer=5′ GAC TCG AGT CGA CAT CGG AGG CTG ATG GGA TGCC 3′ (SEQ ID NO:14); patch primer=3′ CTA AAG ACT CCT CCT AGA CAT CGC CGG CGT ATCG 5′ (SEQ ID NO:17); primers may be used in a ratio of 100 ng 5′ primer/100 ng 3′ primer/1ng patch primer; for details see Section 6, infra. The expression of CNTF/tag may be carried out as described for the expression of recombinant CNTF in U.S. patent application Ser. No. 07/570 651, entitled "Ciliary Neurotrophic Factor, " filed Aug. 20, 1990 by Sendtner et al.

The present invention also provides for a tag which comprises an immunoglobulin molecule, or a portion thereof, e.g. an Fc, F(ab)$_2$, or F(ab)′ fragment of an antibody molecule. The tag should bind to CNTF, and may be a polyclonal or monoclonal antibody.

According to the invention, tagged CNTF may be incubated with cells under conditions which would promote the binding or attachment of CNTF to said cells. In most cases, this may be achieved under standard culture conditions. For example, in a preferred embodiment of the invention, cells may be incubated for about 30 minutes in the presence of tagged CNTF. If the tag is an antibody molecule, it may be preferable to allow CNTF to bind to cells first and subsequently wash cells to remove unbound ligand and then add anti-CNTF antibody tag.

In particular embodiments of the invention, tagged CNTF on the surface of CNTF-responsive cells, hereafter called target cells, may be detected by rosetting assays in which indicator cells that are capable of binding to the tag are incubated with cells bearing CNTF/tag such that they adhere to CNTF/tag on the target cells and the bound indicator cells form rosette-like clusters around CNTF-tag bearing cells. These rosettes may be visualized by standard microscopic techniques on plated cells, or, alternatively, may allow separation of rosetted and non-rosetted cells by density centrifugation. In a preferred specific embodiment of the invention, target cells, such as neuronal cells, may be harvested and plated at a concentration of about 200 cells/well in a multiple well (e.g. 60 well) culture plate in medium such as RPM1 1640 with 10% fetal bovine serum and 2 mM glutamine. Plated cells may be incubated for about 16 to 24 hours at 37° C. in a humidified 5% $CO_2$ atmosphere incubator to allow cells to attach. Next, excess cell culture media may be removed and the cells may be incubated for about 30 minutes at room temperature with tagged CNTF. The cells may then be washed several times with PBS (with calcium and magnesium) supplemented with 1% bovine serum albumin (BSA) to remove unbound ligand and then incubated for about 30 minutes at room temperature with about 10 μg/ml of antibody which recognizes the tag molecule. Cells may then be washed several times with PBS to remove unbound antibody. Then, the target cells (bearing CNTF/tag bound to anti-tag antibody) may be incubated at room temperature for 1 hour with about a 0.2% (v/v) suspension of rosetting indicator cells which bind to the anti-tag antibody (such as indicator cells bearing rabbit-anti-mouse immunoglobulin). The plates may then be washed with PBS and examined under a phase contrast microscope for rosettes. For example, if the anti-tag antibody is produced by a mouse, indicator cells may be produced by coating erythrocytes (such as human O+ erythrocytes) with anti-(mouse immunoglobulin) antibody produced by another species. Indicator cells may be prepared by incubating erythrocytes with anti-immunoglobulin antibody (at a concentration greater than about 1 mg/ml) in the presence of 0.01% $CrCl_3.6H_2O$ diluted in saline according to the procedure of Albino et al. (1981, *J. Exp. Med.* 154:1764–1778). Alternatively, magnetic beads or other methods known in the art may be used.

In alternative embodiments of the invention, tagged CNTF on the surface of target cells may be detected using immunofluorescent techniques in which a molecule which reacts with the tag, preferably an antibody, directly or indirectly produces fluorescent light. The fluorescence may either be observed under a microscope or used to segregate CNTF/tag-bearing cells by fluorescence activated cell sorting techniques. In a preferred specific embodiment of the invention presented by way of example, target cells may be triturated and resuspended in assay buffer containing CNTF/tag (in excess concentration) and sodium azide (0.05%) for about 30 minutes at 4° C. Cells may then be washed three times in assay buffer by centrifugation at 800 rpm for 5 minutes. Cells may then be incubated with anti-tag antibody at a concentration of about 10 μg/ml for about 30 minutes at 4° C., washed as above, and then incubated for about 30 minutes at 4° C. with biotinylated anti-immunoglobulin and streptavidin-Texas Red conjugate. The cells may then be washed, resuspended in mounting solution, coverslipped, and then examined by fluorescent microscopy.

The present invention also provides for methods for detecting other forms of tags, such as chromogenic tags, catalytic tags, etc. The detection methods for any particular tag will depend on the conditions necessary for producing a signal from the tag, but should be readily discernible by one skilled in the art.

Yet another variety of probe which may be used is anti-CNTFR antibody.

According to the invention, CNTFR protein, or fragments or derivatives thereof, may be used as an immunogen to generate anti-CNTFR antibodies. By providing for the production of relatively abundant amounts of CNTFR protein using recombinant techniques for protein synthesis (based upon the CNTFR nucleic acid sequences of the invention), the problem of limited quantities of CNTFR has been obviated.

To further improve the likelihood of producing an anti-CNTFR immune response, the amino acid sequence of CNTFR may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphiphilic helix, amphiphilic sheet, and secondary structure of CNTFR. Alternatively, the deduced amino acid sequences of CNTFR from different species could be compared, and relatively non-homologous regions identified; these non-homologous regions would be more likely to be immunogenic across various species.

For preparation of monoclonal antibodies directed toward CNTFR, any technique which provides for the production of antibody molecules by continuous cell lines in culture may be used. For example, the hybridoma technique originally developed by Kohler and Milstein (1975, *Nature* 256:495–497), as well as the trioma technique, the human B-cell hybridoma technique (Kozbor et al., 1983, *Immunology Today* 4:72), and the EBV-hybridoma technique to produce human monoclonal antibodies (Cole et al., 1985, in "*Monoclonal Antibodies and Cancer Therapy*," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, *Proc. Natl. Acad. Sci. U.S.A.* 80:7308–7312; Kozbor et al., 1983, *Immunology Today* 4:72–79; Olsson et al., 1982, *Meth. Enzymol.* 92:3–16). Chimeric antibody molecules may be prepared containing a mouse antigen-binding domain with human constant regions (Morrison et al., 1984, *Proc. Natl. Acad. Sci. U.S.A.* 81:6851, Takeda et al., 1985, *Nature* 314:452).

Various procedures known in the art may be used for the production of polyclonal antibodies to epitopes of CNTFR. For the production of antibody, various host animals can be immunized by injection with CNTFR protein, or fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and, *Corynebacterium parvum*.

A molecular clone of an antibody to a CNTFR epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

The abovementioned probes may be used experimentally to identify cells or tissues which hitherto had not been shown to express CNTFR. Furthermore, these methods may be used to identify the expression of CNTFR by aberrant tissues, such as malignancies. In additional embodiments, these methods may be used diagnostically to compare the expression of CNTFR in cells, fluids, or tissue from a patient suffering from a disorder with comparable cells, fluid, or tissue from a healthy person. Fluid is construed to refer to any body fluid, but particularly blood or cerebrospinal fluid. A difference in the levels of expression of CNTFR in the patient compared to a healthy person may indicate that the patient's disorder may be primarily or secondarily related to CNTF metabolism. An increase in levels of CNTFR, for example, could either indicate that the patient's disorder is associated with an increased sensitivity to normal levels of CNTF or, alternatively, may suggest that the patient's CNTF levels are low such that the number of receptors is increased by way of compensation. These etiologies may be distinguished from one another by administering CNTF to the patient. If his condition worsens, he may suffer from CNTF hypersensitivity; if it improves, he may be suffering from a CNTF deficiency. CNTF or CNTF antagonist-based therapeutic regimens may be chosen accordingly. Differences in expression can be detected at the protein and/or RNA level; i.e. by measuring amounts of CNTFR protein or CNTFR RNA in a patient relative to those amounts in healthy persons.

The abovementioned probes may also be used to select CNTF-responsive cells for use in assay systems, as described above, or in U.S. application Ser. No.

07/532,285, or according to standard methods of cell selection or cell sorting.

5.6.4. THERAPEUTIC APPLICATIONS

The present invention also provides for methods in which a patient suffering from a disorder, such as neurologic disorder is treated with an effective amount of CNTFR protein, peptide fragment, or derivative of the invention. Therapeutic methods comprising administering CNTFR, CNTFR agonists, CNTFR antagonists (which compete with endogenous CNTF), or anti-CNTFR antibodies are within the scope of the present invention.

The present invention also provides for pharmaceutical compositions comprising CNTFR protein, peptide fragment, or derivative in a suitable pharmacologic carrier.

The CNTFR protein, peptide fragment, or derivative may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

As our understanding of neurodegenerative disease/-neurotrauma becomes clearer, it may become apparent that it would be beneficial to decrease the trophic effect of endogenous CNTF. Therefore, in areas of nervous system trauma, it may be desirable to provide CNTF antagonists, including, but not limited to, cell-free CNTFR which may compete with endogenous cellular receptor for CNTF binding. Under such circumstances, it may be desirable to provide CNTF antagonist locally at the injury site rather than systemically. Use of a CNTFR providing implant may be desirable.

Alternatively, certain conditions may benefit from an increase in CNTF responsiveness. It may therefore be beneficial to increase the number or binding affinity of CNTFRs in patients suffering from such conditions. This could be achieved through gene therapy. Selective expression of recombinant CNTFR in appropriate cells could be achieved using CNTFR genes controlled by tissue specific or inducible promoters or by producing localized infection with replication defective viruses carrying a recombinant CNTFR gene. Conditions which may benefit from increased sensitivity to CNTF include particularly but are not limited to motorneuron disorders including amyotrophic lateral sclerosis, Werdnig-Hoffmann disease, chronic proximal spinal muscular atrophy, and Guillain-Barre syndrome. Such treatment may also be used for treatment of neurological disorders associated with diabetes, Parkinson's disease, Alzheimer's disease, and Huntington's chorea.

Further, it has been shown that the CNTFR gene is expressed in muscle cells (see Section 8, infra). Accordingly, the present invention provides for methods of treating muscle cell disorders comprising administering to a patient in need of such treatment (i) a nucleic acid molecule comprising a nucleotide sequence which encodes CNTFR or a functional portion thereof, or (ii) CNTF. Muscle cell disorders which may benefit from such treatment include but are not limited to the following progressive muscular dystrophies: Duchenne, Becker, Emery-Dreifuss, Landouzy-Dejerine, scapulohumeral, limb-girdle, Von Graefe-Fuchs, oculopharyngeal, myotonic and congenital. In addition, such molecules may be of use in the treatment of congenital (central core, nemaline, centronuclear and congenital fiber-type dysproportion) and acquired (toxic, inflammatory) myopathies. The present invention further provides for a method of treating a muscle cell disorder comprising administering to the patient an effective amount of CNTF protein or an active portion thereof.

In a further embodiment of the invention, patients that suffer from an excess of CNTFR, hypersensitivity to CNTF, excess CNTF, etc. may be treated by administering an effective amount of anti-sense RNA or antisense oligodeoxyribonucleotides corresponding to the CNTFR gene coding region thereby decreasing expression of CNTFR.

6. EXAMPLE: EXPRESSION CLONING OF THE CILIARY NEUROTROPHIC FACTOR RECEPTOR

6.1. MATERIALS AND METHODS

6.1.1. CONSTRUCTION OF A CNTF-RECEPTOR EXPRESSION LIBRARY

SH-SY5Y cells (originally obtained from Dr. June Biedler) were used as a source of mRNA for construction of a cDNA library using the pCMX expression vector (described in copending U.S. patent application Ser. No. 07/678,408 filed concurrently herewith, see supra), a derivative of the pCDM8 vector (Seed, 1987, Nature 329:840-842). Inserts for the cDNA library were selected on an agarose gel for sizes larger than 1 kb.

6.1.2. "PANNING" METHOD

The "panning" method developed by Seed and Aruffo (1987, Proc. Natl. Acad. Sci. U.S.A. 84:3365-3369) was modified as follows: instead of incubating the cells with antibodies recognizing the receptor, cells were incubated first with CNTF/myc (1 µg/ml) on ice for 30 minutes, spun through PBS/2% Ficoll to remove excess ligand, and then incubated with 9E10 antibody obtained from Oncogene Sciences, Manhasset, N.Y. for 30 minutes on ice. This was followed by another spin through PBS/2% Ficoll and "panning" on plates coated with anti-myc peptide mouse monoclonal antibody obtained from Sigma. The plates were prepared as follows: bacteriological 60 mm plates (Falcon 1007 or the equivalent), or 10 cm dishes such as Fisher 8-757-12 were coated with anti-myc mouse monoclonal antibody, diluted to 10 micrograms per ml in 50 mM Tris HCl pH 9.5. 3 ml of antibody was used to coat each 6 cm dish or 10 ml was used per 10 cm dish; plates were exposed to antibody for about 1.5 hrs, then antibody was removed to the next dish, allowed to stand for 1.5 hrs, and then removed again to a third dish. Plates were washed three times with 0.15 M NaCl (a wash bottle is convenient for this), and incubated with 3 ml 1 mg/ml BSA in PBS overnight. In particular "panning" was performed as follows: cells were cultured in 100 mm dishes. Medium was aspirated from each dish, and 2 ml PBS/0.5 mM EDTA/0.02% azide was added and the mixture was incubated at 37° for 30 min to detach cells from the dish. The cells were triturated vigorously with a short pasteur pipet, collected from each dish in a centrifuge tube, and spun 4 min at a setting of 2.5 (200×g). Cells were resuspended in 0.5-1.0 ml PBS/EDTA/azide/5% FBS and incubated with CNTF/myc for 30 min on ice. An equal volume of PBS/EDTA/azide was added, layered carefully on 3 ml PBS/EDTA/azide/2% Ficoll, spun 4 min at a setting of 2.5, and the supernatant was aspirated in one smooth movement. The cells were then incubated with 9E10 antibody for 30 minutes on ice, and the spin through PBS/EDTA/azide/2% Ficoll was repeated. The cells were taken up in 0.5 ml PBS/EDTA/azide and aliquots were added to anti-myc mouse monoclonal antibody-coated dishes containing 3 ml PBS/EDTA/azide/5% FBS. Cells were added from at most two 60 mm dishes to one 60 mm antibody coated plate, and allowed to sit at room temperature 1–3 hours. Excess cells not adhering to dish were removed by gentle washing with PBS/5% serum or with medium (2 or 3 washes of 3 ml were usually sufficient).

6.1.3. IDENTIFICATION OF CLONES CONTAINING THE CILIARY NEUROTROPHIC FACTOR RECEPTOR GENE

Plasmid DNA from the expression library was transfected into COSM5 cells (approximately 250–500 ng per 100 mm dish; 2 dishes were transfected), using DEAE/chloroquine according to standard procedures. Two days after transfection, cells were detached from their dishes and subjected to the Aruffo/Seed panning procedure modified as described After washing nonadhering cells from the plates, Hirt supernatants (Hirt, 1967, *J. Mol. Biol.* 26:365–369) were prepared, and plasmid DNA was precipitated in the presence of 10–20 μg of tRNA. The resulting DNA was introduced into DH10B bacteria (Electromax, BRL) by electroporation according to the manufacturer's instructions. Cultures grown from the electroporated bacteria were used to prepare plasmid DNA for another round of transfection and panning; a plate of COS cells transfected with this plasmid DNA clearly revealed a large number of COS cells expressing the CNTFR by an indirect iodinated-antibody binding assay (see FIG. 1B for representative data, see below for assay methods). After a second round of panning/plasmid DNA isolation/electroporation on these transfectants, the bacterial transformants resulting from the electroporation step were plated out on ampicillin plates. Individual bacterial colonies were picked, and plasmid DNA prepared from each of the clones was transfected individually into COS cells for assay. Out of 15 plasmids tested, 14 resulted in transfected COS cells expressing CNTF binding sites by a variety of assays, including the indirect antibody binding assay and fluorescence activated cell sorting (FACS) analysis described infra.

6.1.4 DIRECT $^{125}$I-hCNTF BINDING ASSAY

COS cells were transfected with plasmid DNA from the library, the enriched library, or individual clones. After 48 hours, the media was removed and replaced with 0.25 ml of binding buffer (RPM1 1640 with 10% FBS and 0.1% NAN3) containing 125I-hCNTF alone or with unlabelled hCNTF. Incubations with $^{125}$I-hCNTF were for 60 minutes at room temperature. After incubations were complete, the $^{125}$IhCNTF solution was removed and the cells were washed three times with 1.0 ml of binding buffer and then lysed with 0.25 ml of 0.1N NaOH. This lysate was transferred to a 12×75 mm polystyrene tube and placed in a gamma counter. Non-specific binding was determined by the addition of at least 100 fold excess unlabelled hCNTF. After the last wash the plates were autoradiographed.

6.1.5. FLUORESENCE ACTIVATED CELL-SORTING ANALYSIS

Transfected COS cells were incubated sequentially with CNTF/myc, 9E10 antibody, and FITC-labelled goat anti-mouse antibody. Then they were detached from dishes and subjected to FACS analysis. The results of transfections with a negative and positive plasmid are depicted in FIG. 1D; COS cells transfected with a CNTF-receptor expressing plasmid contain a large subpopulation displaying greatly increased fluorescence by this assay.

6.1.6. IODINATION OF hCNTF

10 μg hCNTF (560 μg/ml in 10 mM NaPO4pH7.4) was iodinated with 1 mCi $^{125}$INa using lactoperoxidase 6 ng/μl (Sigma) for 15 minutes at 20° C. After 15 minutes the reaction was quenched with an equal volume of buffer containing 0.1M NaI, 0.1% BSA and 0.1% cytochrome C, 0.3% HOAc, 0.05% phenol red and 0.02% NAN3. Aliquots were removed for determination of TCA precipitatable counts. The remainder was loaded onto a BioRad PD—10 biogel column equilibrated with 0.05M NaPO4, 0.1M NaCl, 0.5 mg/ml protamine sulfate and 1 mg/ml BSA. Fractions were collected and TCA precipitatable counts determined.

6.1.7. SEQUENCING OF CNTFR

Sequencing was performed using a kit (U.S. Biochemical) for dideoxy double stranded DNA using Sequenase ™, according to the manufacturer's instructions

6.1.8. INDIRECT $^{125}$I GOAT ANTI-MOUSE ANTIBODY BINDING ASSAY

COS cells were transfected with plasmid DNA from the library, the enriched library, or individual clones. After 48 hours, cells were incubated sequentially for 30 minutes on ice with PBS (with Ca, Mg)/5% FBS containing:

1) 1 μg/ml CNTF-myc
2) 10 μg/ml 9E10;

$^{125}$I goat anti-mouse antibody (GaM) (0.5–1 μCi/ml). Cells were washed 3×5 minutes in PBS/5% FBS after each step. After the last wash, the plates were autoradiographed.

For the individual clones, a quantitative estimate of total radioactivity bound was made with a hand-held gamma counter.

6.2. RESULTS AND DISCUSSION

6.2.1. RESTRICTION ANALYSIS

On restriction analysis, the 14 positive clones fell into four classes:

a) I2=I7 (2 kb)
b) I1=I5=I6 (2 kb)
c) I4=I8=I9=I11=I14=I15 (4 kb)
d) I10=I12=I13 (1.6 kb)
(I3 was negative))

Members of each class produced an identical pattern of bands on digestion with the enzyme PstI. Further restriction analysis revealed that the four classes of clones overlapped, and preliminary sequence data confirmed that they shared overlapping sequences at their 5' ends. Curiously, class (b) proved to have its insert in the wrong orientation in the vector with respect to the eukaryotic promoter element. As can be seen from Table I, these clones were low expressors relative to the other clones. Transcription in these clones may arise from a weak cryptic promoter in the region downstream of the vector's polylinker.

6.2.2. IN VITRO TRANSCRIPTION AND TRANSLATION

To characterize the proteins coded for by the four classes of clones, they were all transcribed from the T7 promoter in the 5' region of the vector polylinker. After in vitro translation, the products were electrophoresed on a polyacrylamide gel. Class (a) produced no protein, since it is in the wrong orientation with respect to the T7 promoter. The other three classes all produced proteins of identical sizes (approximately 42 kd), verifying that they encoded the same protein.

TABLE I

| Quantitation of $^{125}$I-GaM binding in CNTFR clones. | |
|---|---|
| Clone | CPM bound |
| I1 | 2000 |
| I2 | 8500 |
| I3 | 600 |
| I4 | 9000 |
| I5 | 2000 |
| I6 | 1600 |
| I7 | 6000 |
| I8 | 7500 |
| I9 | 7000 |
| I10 | 4500 |
| I11 | 7000 |
| I12 | 5000 |
| I13 | 8000 |
| I14 | 10000 |
| I15 | 8000 |
| Negative Control | 500 |
| Background | 250 |

6.2.3. BINDING ANALYSIS WITH CNTF

The results of the indirect CNTF-myc binding assay using 9E10 anti-myc antibody and $^{125}$I goat anti-mouse antibody are shown in FIGS. 1B and 1C as well as in Table I. In FIG. 1B, the plate on the left results from transfection of the unenriched library, while the plate on the right is from transfection of the enriched library plasmid DNA rescued after one round of panning (using approximately the same amount of DNA as for the unenriched library). Note the large number of dark spots seen only in the plate on the right, each representing a single COS cell expressing CNTF-myc binding site detected by radioautography.

For the individual positive clones discussed in Section 6.2.1, a quantitative estimate of total radioactivity was made with a hand-held gamma counter. The results of this assay for the individual clones I1-I15 are shown in Table I and demonstrate that 14 out of 15 clones express CNTF binding sites, as determined by indirect antibody binding assay. In addition, fragments of the plates from some of the individual clones were autoradiographed, as shown in FIG. 1C(i-ii).

A second demonstration of indirect binding utilized CNTF-myc followed by 9E10 antibody, FITC-labelled goat anti-mouse antibody, and FACS analysis, as shown in FIG. 1D. COS cells transfected with positive clones demonstrated a 100-fold increase in expression of CNTFR as compared with cells transfected with negative clones.

The indirect binding data obtained using CNTF-myc was verified using direct $^{125}$I-CNTF binding, as shown in Table II. The receptor expressed on transfected COS cells specifically binds to iodinated CNTF as well as to the CNTF-myc ligand, as did the SH-SY5Y cells from which the CNTFR was cloned. Each transfected COS cell expresses about 30-fold more receptor per cell than SH-SY5Y cells.

TABLE II

| | Binding Analysis With Iodinated CNTF | | | |
|---|---|---|---|---|
| | COS I2 | | SH-SY5Y | |
| Conc. $^{125}$I-CNTF | Specific cpm bound | cpm/cell* | Specific cpm bound | cpm/cell |
| 2.16 nM | 1412 | $2.17 \times 10^{-2}$ | 1284 | $4.28 \times 10^{-3}$ |

Monolayer binding assays were performed in 24 well culture plates using $3 \times 10^5$ SH-SY5Y cells/well or $6.5 \times 10^4$ COS cells/well. Specific cpm bound was calculated by subtracting cpm bound in the presence of 1000-fold excess of unlabelled CNTF from the cpm bound only in the presence of $^{125}$I-CNTF at the concentration indicated. No specific binding was detected in untransfected COS cells.

*COS cells were assayed 48 hours after transfection by DEAE Dextran in which typically only 20-40% of the cells are transfected. Assuming 20% COS cells are transfected, the specific cpm bound indicate that each transfected COS cell expresses about 30-fold more receptors per cell than SH-SY5Y cells.

6.2.4. SEQUENCE OF CNTFR AND HOMOLOGY TO OTHER GROWTH FACTOR RECEPTORS

The CNTFR contains motifs which are shared with a variety of other receptors. The extracellular portion of the CNTFR contains both an "immunoglobulin" domain at its N-terminus, as well as a "cytokine receptor" domain which is separated from the "immunoglobulin" domain by a short hinge region. Although many receptors have homology to either the "immunoglobulin" [SEQ ID NO:3 (hCNTFR); 4 (hhIL6R); 4 (hCEA); 5 (PDGFR); 6 (CSF-1R); 7 (alpha 1-β-GP)] or "cytokine receptor" [SEQ ID NO:2 (hCNTFR); 8 (hIL6R); 9 (rPRLR); 10 (mEPOR); 11 (hIL2R); 14 (mIL4R); 13 (hGM-CSFR)] domains (FIGS. 3A-3B), only one receptor-the IL-6 receptor-shares the same particular arrangement of these domains with the CNTFR (FIGS. 3A-3B and 4). The IL-6 receptor is thus the protein most related to the CNTFR (FIG. 4). Interestingly, the IL-6 receptor is also similar to the CNTFR in that it has a very short intracytoplasmic domain which is apparently not required for initiating responses upon IL-6 binding (Hibi et al., 1990, Cell 63:1149-1157). Recently, a novel signal transducer for the IL-6 receptor, termed gp 130, was molecularly cloned. This transducer does not bind IL-6 by itself, but it does confer high affinity binding to the IL-6 receptor and it is required to transduce the IL-6 signal (Hibi et al., 1990, Cell 63:1149-1157). Our cloning of the CNTFR reveals that it shares important features with the IL-6 receptor that are not found in other known receptors, thus defining a new family of receptors. The similarities between IL-6R and CNTFR suggest that CNTFR is likely to utilize the same signal transducer as the IL-6 receptor, or a related molecule. Finally, the identification of CNTFR-related receptors should aid in the identification of novel ligands that would bind to these receptors.

7. EXAMPLE: TISSUE LOCALIZATION OF MESSAGE FOR CNTFR

7.1. MATERIALS AND METHODS

7.1.1. CNTFR PROBE PREPARATION

Molecular cloning of the coding region for hCNTFR into the pCMX expression vector is described in U.S. patent application entitled "Mammalian Expression Vector" filed concurrently herewith, and the resulting expression vector (hhIL6R); 4 (hCEA); 5 (PDGFR); 6 (CSF-1R); 7 (alpha 1-β-GP)] or "cytokine receptor" [SEQ ID NO:2 (hCNTFR); 8 (hIL6R); 9 (rPRLR); 10 (mEPOR); 11 (hIL2R); 14 (mIL4R); 13 (hGM-CSFR)] domains (FIG. 3), only one receptor-the IL-6 receptor-shares the same particular arrangement of these domains with the CNTFR (FIGS. 3 and 4). The IL-6 receptor is thus the protein most related to the CNTFR (FIG. 4). Interestingly, the IL-6 receptor is also similar to the CNTFR in that it has a very short intracytoplasmic domain which is apparently not required for initiating responses upon IL-6 binding (Hibi et al., 1990, *Cell* 63:1149-1157). Recently, a novel signal transducer for the IL-6 receptor, termed gp 130, was molecularly cloned. This transducer does not bind IL-6 by itself, but it does confer high affinity binding to the IL-6 receptor and it is required to transduce the IL-6 signal (Hibi et al., 1990, *Cell* 63:1149-1157). Our cloning of the CNTFR reveals that it shares important features with the IL-6 receptor that are not found in other known receptors, thus defining a new family of receptors. The similarities between IL-6R and CNTFR suggest that CNTFR is likely to utilize the same signal transducer as the IL-6 receptor, or a related molecule. Finally, the identification of CNTFR-related receptors should aid in the identification of novel ligands that would bind to these receptors.

7. EXAMPLE: TISSUE LOCALIZATION OF MESSAGE FOR CNTFR

7.1. MATERIALS AND METHODS

7.1.1. CNTFR PROBE PREPARATION

Molecular cloning of the coding region for hCNTFR into the pCMX expression vector is described in U.S. patent application entitled "Mammalian Expression Vector" filed concurrently herewith, and the resulting expression vector indicate that CNTF possesses not only neurotrophic activity, but myotrophic activity as well, and may explain the involvement of both the central nervous system and muscle in certain disorders, such as Duchennes muscular dystrophy and congenital myotonic dystrophy, in which patients may suffer from mental retardation. Expression of CNTFR in muscle suggests CNTF may have a role in muscle physiology. Thus, in addition to action on neurons, CNTF may have important action in muscle such as functioning as a myotrophic agent, or otherwise effect muscle development and/or differentiation.

8. EXAMPLE: EVIDENCE THAT THE CNTF RECEPTOR IS LINKED TO THE CELL SURFACE VIA A GLYCOSYLPHOSPHATIDYLINOSITOL (GPI) LINKAGE

8.1. MATERIALS AND METHODS

SH-SY5Y cells were cultured in a 24-well plate (Falcon) in RPMI supplemented with 10% inactivated fetal bovine serum. For experiments in which phospholipase (and control) treatments were done prior to CNTF-binding, the media was aspirated, cells were rinsed twice in PBS(+Ca/Mg), and then incubated with PBS(+Ca/Mg) supplemented with or without phosphatidylinositol-specific phospholipase (PI-PLC) at final concentration of 500 mU/ml (purchased from Boehringer Mannheim, catalogue #1143-069) for 45 minutes at 37° C. Cells were then washed three times with binding buffer (PBS(+Ca/Mg) and 5% fetal bovine serum) and then incubated with 250 microliters binding buffer containing iodinated CNTF (approximately 100 picomolar) with or without a thousand-fold excess of unlabelled CNTF for 30 minutes at room temperature. For experiments in which the iodinated CNTF was bound prior to PI-PLC treatment, cells were first incubated in binding buffer containing iodinated CNTF with or without excess unlabelled CNTF at 37° C. for 45 minutes. Cells were then washed two times with PBS(+Ca/Mg) and then incubated for 45 minutes with PBS(+Ca/Mg) supplemented with or without PI-PLC (final concentration 500 mU/ml). Cells were then rinsed three times with binding buffer. In all cases cells were solubilized prior to counting in 0.1N NaOH, and then counted.

8.2. RESULTS AND DISCUSSION

The sequence of the CNTF receptor revealed that the encoded protein ended within a hydrophobic region that followed the extra-cytoplasmic domains, without any apparent stop transfer sequence or intra-cytoplasmic domain. This structure seemed reminiscent of the C-terminals found on membrane proteins which lack transmembrane domains and are attached to the cell surface via GPI-linkages (Ferguson and Williams, 1988). Thus, experiments were performed to test whether the CNTF receptor was linked to the cell surface via a GPI-linkage. As shown in Table III, treatment of SH-SY5Y cells with PI-PLC completely eliminated the ability of SH-SY5Y cells to subsequently bind CNTF, consistent with the notion that the CNTF receptor is linked to the cell surface via a GPI-linkage. However, CNTF already bound to SH-SY5Y cells cannot be released by PI-PLC treatment (Table III). Interestingly, a soluble form of the IL-6 receptor can tightly associate with a second membrane protein (GP130) required for IL-6 signal transduction. Thus, prevention of CNTF receptor release by prior binding to CNTF may be due to an association between the CNTF, its receptor, and its signal transducer (GP130 or a GP130 analog). Alternatively, CNTF-binding may alter the structure of the CNTF receptor, making it less susceptible to PI-PLC (several GPI-linked proteins have PI-PLC resistant forms).

The finding that the CNTF receptor is attached to the cell surface via a GPI-linkage has important ramifications, It represents the first known growth factor receptor to be linked to the membrane in this fashion, raising the possibility that additional receptors may be GPI-linked. Because several proteins have both GPI-linked forms as well as forms that contain conventional transmembrane domains, our findings raise the possibility that the CNTF receptor has an alternative C-terminus that could encode a transmembrane domain, and similarly that the IL-6 receptor has a GPI-linked form. The GPI-linked forms of growth factor receptors may be able to utilize novel mechanisms of receptor regulation and release. For example, down-regulation of surface receptors could rapidly occur by releasing the GPI-linked receptors by activating extra-cytoplasmic phospholipase activities. These released receptors might also act on other cells, either alone or when bound to CNTF in much the same way that soluble IL-6 receptor has been shown to bind IL-6 and activate cells expressing GP130.

The possibility that release of CNTF receptors using PI-PLC could block CNTF action may have important implications. It could be used to verify that observed effects of CNTF are due to the cloned CNTF receptor. Therapeutically, PI-PLC could be used to release CNTF receptors and possibly block CNTF action in cases where CNTF activity is thought to be detrimental.

If the CNTF-blockable PI-PLC release of the CNTF receptor is due to the formation of a tertiary complex between the CNTF, its receptor, and the potential signal transducing protein, then this feature of the receptor could be used to define and molecularly clone the transducing molecule.

TABLE III

Analysis Of PI-PLC Treatment On CNTF Binding To SH-SY5Y Cells

|  | CPM Bound | |
| --- | --- | --- |
|  | No Cold Excess | Cold Excess |
| Pre-Treat with PI-PLC | | |
| No PI-PLC | 1440 | 370 |
| With PI-PLC | 420 | 310 |
| Bind CNTF Before PI-PLC | | |
| No PI-PLC | 1250 | 310 |
| With PI-PLC | 1060 | 300 |

9. DEPOSIT OF MICROORGANISM

The following deposit has been made on Mar. 26, 1991 with The Agricultural Research Culture Collection (NRRL), North University Street, Peoria, Ill., 61604:

*E. coli* carrying plasmid pCMX-hCNTFR (I2), an expression plasmid comprising hCNTFR encoding sequences, assigned accession number B-18789.

Various references are cited herein, the disclosures of which are incorporated by reference in their entireties.

The present invention is not to be limited in scope by the construct deposited or the embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the scope of the appended claims.

---

What is claimed is:

1. Isolated and purified CNTF receptor comprising the amino acid sequence as depicted in FIG. 2 (SEQ ID no. 1)

* * * * *